(12) United States Patent
Kassab

(10) Patent No.: US 8,945,039 B2
(45) Date of Patent: Feb. 3, 2015

(54) DEVICES, SYSTEMS, AND METHODS FOR ORGAN RETROPERFUSION

(75) Inventor: Ghassan S. Kassab, Zionsville, IN (US)

(73) Assignee: CVDevices, LLC, San Diego, CA (US)

(*) Notice: Subject to any disclaimer, the term of this patent is extended or adjusted under 35 U.S.C. 154(b) by 54 days.

(21) Appl. No.: 13/221,514

(22) Filed: Aug. 30, 2011

(65) Prior Publication Data

US 2011/0313341 A1 Dec. 22, 2011

Related U.S. Application Data

(63) Continuation-in-part of application No. 13/092,803, filed on Apr. 22, 2011, which is a continuation-in-part of application No. 13/125,512, filed as application No. PCT/US2008/087863 on Dec. 19, 2008.

(51) Int. Cl.
| | | |
|---|---|---|
| *A61M 5/00* | (2006.01) | |
| *A61M 27/00* | (2006.01) | |
| *A61B 5/0215* | (2006.01) | |
| *A61M 1/36* | (2006.01) | |
| A61M 25/00 | (2006.01) | |
| A61M 25/10 | (2013.01) | |

(52) U.S. Cl.
CPC ............ *A61M 27/00* (2013.01); *A61B 5/02152* (2013.01); *A61M 1/3653* (2013.01); *A61M 25/007* (2013.01); *A61M 2025/1052* (2013.01); *A61M 2025/1097* (2013.01); *A61M 2205/3523* (2013.01); *A61M 2205/3561* (2013.01)
USPC .................................. 604/9; 604/8; 604/4.01

(58) Field of Classification Search
USPC ................. 604/8, 9, 27–28, 30, 4–6.161, 301
See application file for complete search history.

(56) References Cited

U.S. PATENT DOCUMENTS

| 4,318,401 A | 3/1982 | Zimmerman |
|---|---|---|
| 4,957,110 A | 9/1990 | Vogel et al. |

(Continued)

FOREIGN PATENT DOCUMENTS

| JP | U-H06-021648 | 3/1994 |
|---|---|---|
| WO | WO 2008/144382 | 11/2008 |

OTHER PUBLICATIONS

PCT/US2008/087863, PCT Search Report dated Feb. 13, 2009.

(Continued)

*Primary Examiner* — Tatyana Zalukaeva
*Assistant Examiner* — Benjamin Klein
(74) *Attorney, Agent, or Firm* — Reichel IP LLP; Mark C. Reichel; Natalie J. Dean

(57) ABSTRACT

Devices, systems, and methods for organ retroperfusion. In at least one embodiment of a method of organ perfusion of the present disclosure, the method comprises the steps of positioning at least part of a first catheter having a cannula within an artery of a patient, the first catheter configured to permit arterial blood to flow therethrough and further configured to permit a portion of the arterial blood to flow through the cannula, positioning at least part of a second catheter within a vein of the patient at or near a target organ, the second catheter configured to receive some or all of the portion of the arterial blood, and connecting the cannula of the first catheter to a portion of the second catheter so that some or all of the portion of the arterial blood flowing through the cannula is provided into the vein to treat a condition or disease of the target organ.

23 Claims, 21 Drawing Sheets

(56) References Cited

U.S. PATENT DOCUMENTS

| | | | |
|---|---|---|---|
| 5,273,534 A | 12/1993 | Knoepfler | |
| 5,494,822 A * | 2/1996 | Sadri | 435/284.1 |
| 5,511,553 A | 4/1996 | Segalowitz | |
| 5,655,548 A | 8/1997 | Nelson et al. | |
| 6,110,139 A * | 8/2000 | Loubser | 604/30 |
| 6,186,972 B1 | 2/2001 | Nelson et al. | |
| 6,241,699 B1 | 6/2001 | Suresh et al. | |
| 7,004,925 B2 | 2/2006 | Navia et al. | |
| 7,004,926 B2 | 2/2006 | Navia et al. | |
| 7,473,237 B2 * | 1/2009 | Navia et al. | 604/6.13 |
| 7,819,856 B2 | 10/2010 | Bates | |
| 8,313,452 B2 * | 11/2012 | Franco Nardo et al. | 604/6.14 |
| 8,784,355 B2 * | 7/2014 | Criado et al. | 604/9 |
| 2003/0125798 A1 | 7/2003 | Martin | |
| 2003/0181843 A1 | 9/2003 | Bibber et al. | |
| 2005/0267323 A1 * | 12/2005 | Dorros et al. | 600/16 |
| 2006/0184088 A1 | 8/2006 | Van Bibber et al. | |
| 2007/0010781 A1 | 1/2007 | Vijay | |
| 2008/0234658 A1 | 9/2008 | Kassab et al. | |
| 2009/0018455 A1 * | 1/2009 | Chang | 600/504 |

OTHER PUBLICATIONS

PCT/US2008/087863, PCT Written Opinion dated Feb. 13, 2009.

* cited by examiner

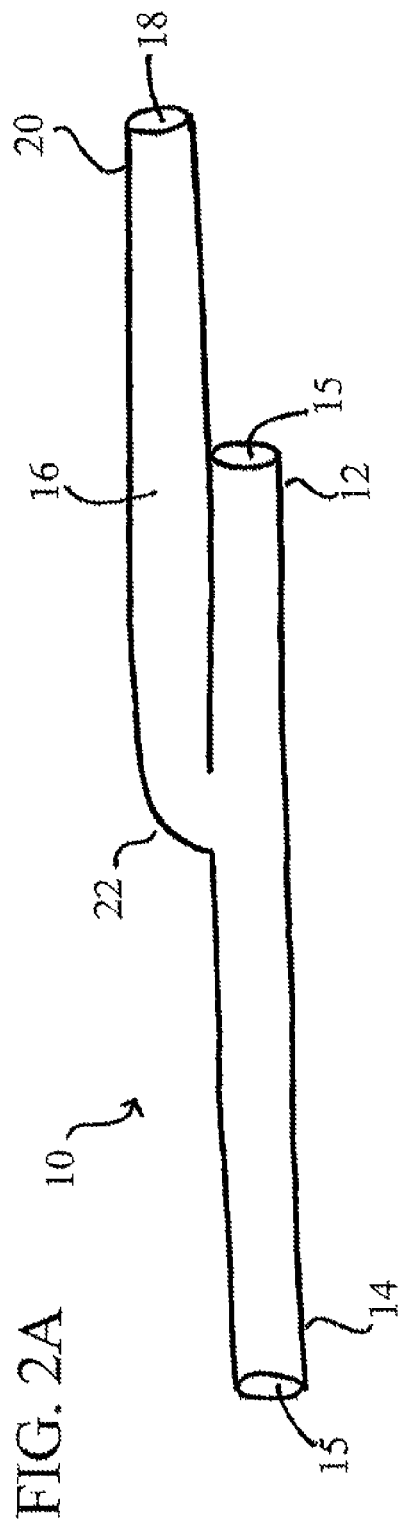
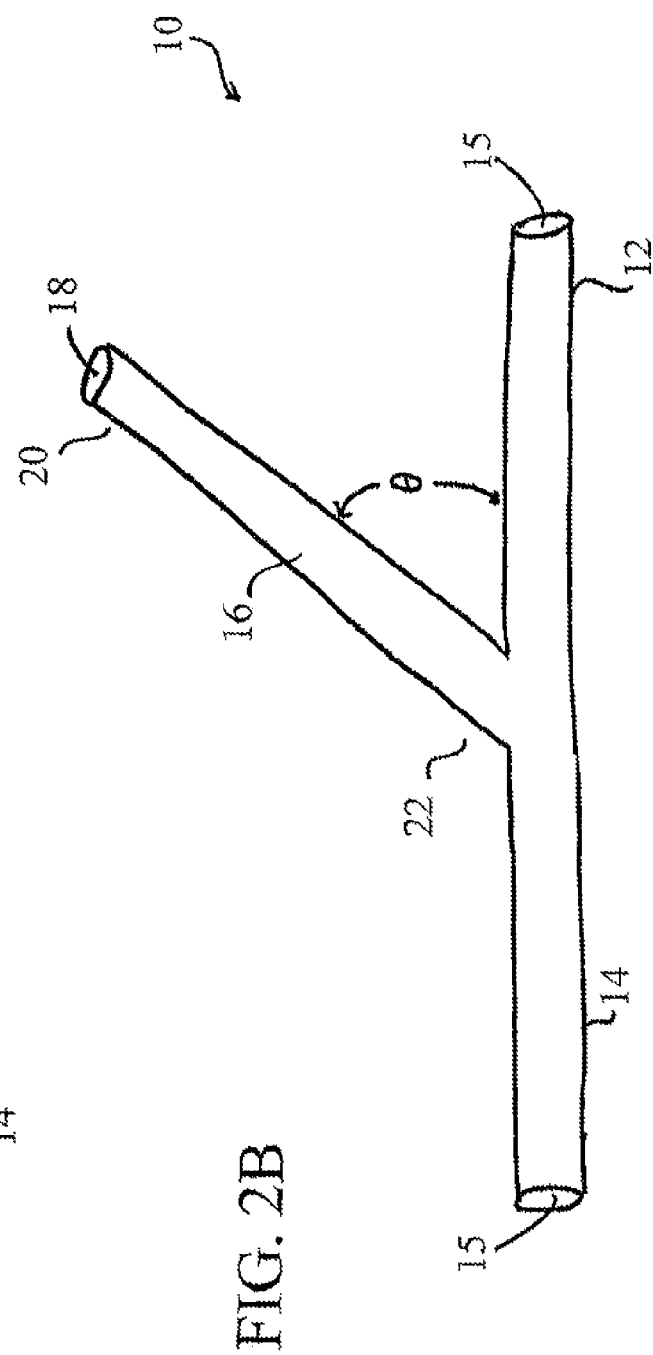
FIG. 2A
FIG. 2B

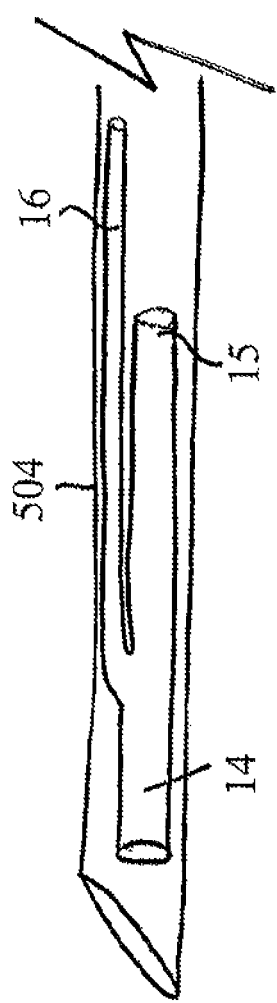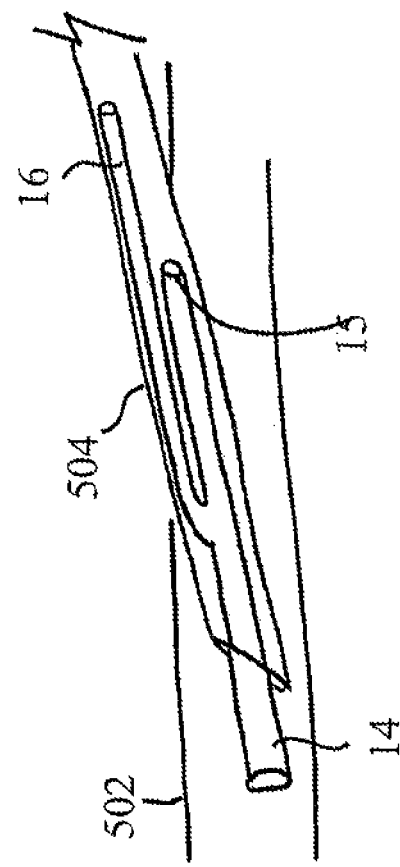

DEVICES, SYSTEMS, AND METHODS FOR ORGAN RETROPERFUSION

PRIORITY

The present U.S. continuation-in-part application is related to, and claims the priority benefit of, U.S. Nonprovisional patent application Ser. No. 13/092,803, filed Apr. 22, 2011, which is related to, claims the priority benefit of, and is a U.S. continuation-in-part application of, U.S. Nonprovisional patent application Ser. No. 13/125,512, filed Apr. 21, 2011, which is related to, claims the priority benefit of, and is a U.S. §371 national stage entry of, International Patent Application Serial No. PCT/US2008/087863, filed Dec. 19, 2008. The contents of each of these applications are hereby incorporated by reference in their entirety into this disclosure.

BACKGROUND

While direct surgical and percutaneous revascularization through procedures such as a percutaneous transluminal coronary angioplasty ("PTCA") or coronary artery bypass grafting ("CABG") remain the mainstay of treatment for patients with angina and coronary artery disease ("CAD"), there are many patients that are not amenable to such conventional revascularization therapies. Because of this, much effort has been made to find alternative methods of revascularization for ischemic cardiac patients who are not candidates for revascularization by conventional techniques. Such patients are generally identified as "no-option" patients because there is no conventional therapeutic option available to treat their condition. As described in detail herein, the present disclosure provides various embodiments of devices to address such chronic conditions.

In addition, and as described in detail herein, the present disclosure provides various embodiments of devices that can be used acutely to treat patients with a number of conditions, such as S-T segment elevated myocardial infarction (STEMI) or cardiogenic shock or patients who require high risk percutaneous coronary intervention, until they can receive more traditional therapy.

Currently, there are multiple specific conditions for which conventional revascularization techniques are known to be ineffective as a treatment. Two specific examples of such cardiac conditions include, without limitation, diffuse CAD and refractory angina. Furthermore, a percentage of all patients diagnosed with symptomatic CAD are not suitable for CABG or PTCA. In addition and for various reasons discussed below, diabetic patients—especially those with type 2 diabetes—exhibit an increased risk for CAD that is not effectively treated by conventional revascularization techniques.

There is currently little data available on the prevalence and prognosis of patients with symptomatic CAD that is not amenable to revascularization through conventional methods. However, one study indicated that out of five hundred (500) patients with symptomatic CAD who were considering direct myocardial revascularization and angiogenesis, almost twelve percent (12%) were not suitable for CABG or PTCA for various reasons. Furthermore, in general, patients with atherosclerotic involvement of the distal coronary arteries have high mortality and morbidity. For example, a study conducted on patients indicated that, one (1) year after being diagnosed with atherosclerotic involvement of the distal coronary arteries, 39.2% of such patients had a cardiac-related death, 37.2% had an acute myocardial infarction, and 5.8% had developed congestive heart failure. Overall, 82.2% of the patients with atherosclerotic involvement of distal coronary arteries had developed or experienced a significant cardiac event within one (1) year.

A. Diffuse CAD and Refractory Angina

CAD is typically not focal (i.e. limited to one point or a small region of the coronary artery), but rather diffused over a large length of the entire vessel, which is termed "diffuse CAD." Several studies indicate that patients with a diffusely diseased coronary artery for whom standard CABG techniques cannot be successfully performed constitute about 0.8% to about 25.1% of all patients diagnosed with CAD. Furthermore, it is believed that diffuse CAD is much more common than conventionally diagnosed because it is often difficult to detect by an angiogram due to the two-dimensional views.

Practitioners have realized that the quality of a patient's distal coronary arteries is one of the critical factors related to a successful outcome of a surgical revascularization. As previously indicated, there is considerable evidence that CABG for vessels having diffuse CAD results in a relatively poor outcome. In fact, studies have indicated that diffuse CAD is a strong independent predictor of death after a CABG procedure. Further, as previously noted conventional revascularization techniques have also proven ineffective on a subgroup of patients with medically refractory angina. In line with the aforementioned reasoning, this is likely because patients with medically refractory angina have small or diffusely diseased distal vessels that are not amenable to conventional revascularization therapies. Accordingly, patients exhibiting diffuse CAD or medically refractory angina are often considered no-option patients and not offered bypass surgery, PTCA, or other conventional procedures.

B. Diabetes as a Risk Factor

Diabetes is an important risk factor for the development of CAD, diffuse or asymptomatic, and it has been estimated that approximately seventy-five percent (75%) of the deaths in diabetic patients are likely attributed to CAD. It is estimated that 16 million Americans have diabetes, without only 10 million being diagnosed. Patients with diabetes develop CAD at an accelerated rate and have a higher incidence of heart failure, myocardial infarction, and cardiac death than non-diabetics.

According to recent projections, the prevalence of diabetes in the United States is predicted to be about ten percent (10%) of the population by 2025. Further, the increasing prevalence of obesity and sedentary lifestyles throughout developed countries around the world is expected to drive the worldwide number of individuals with diabetes to more than 330 million by the year 2025. As may be expected, the burden of cardiovascular disease and premature mortality that is associated with diabetes will also substantially increase, reflecting in not only an increased amount of individuals with CAD, but an increased number of younger adults and adolescents with type 2 diabetes who are at a two- to four-fold higher risk of experiencing a cardiovascular-related death as compared to non-diabetics.

In addition to developing CAD at an accelerated rate, CAD in diabetic patients is typically detected in an advanced stage, as opposed to when the disease is premature and symptomatic. Consequently, when diabetic patients are finally diagnosed with CAD they commonly exhibit more extensive coronary atherosclerosis and their epicardial vessels are less amendable to interventional treatment, as compared to the non-diabetic population. Moreover, as compared with non-diabetic patients, diabetic patients have lower ejection fractions in general and therefore have an increased chance of suffering from silent myocardial infarctions.

C. No-Option Patients

Some studies have shown that two-thirds (⅔rds) of the patients who were not offered bypass surgery, because of diffuse CAD or otherwise, either died or had a non-fatal myocardial infarction within twelve (12) months. Furthermore, patients diagnosed with diffuse CAD ran a two-fold increased risk of in-hospital death or major morbidity, and their survival rate at two (2) years was worse than those patients who exhibited non-diffuse CAD or other complicating conditions. As previously indicated, the majority of these patients are considered no-option patients and are frequently denied bypass surgery as it is believed that CABG would result in a poor outcome.

Due to the increasing numbers of no-option patients and a trend in cardiac surgery towards more aggressive coronary interventions, a growing percentage of patients with diffuse CAD and other no-option indications are being approved for coronary bypass surgery because, in effect, there are no other meaningful treatment or therapeutic options. Some effects of this trend are that the practice of coronary bypass surgery has undergone significant changes due to the aggressive use of coronary stents and the clinical profiles of patients referred for CABG are declining. As such, performing effective and successful coronary bypass surgeries is becoming much more challenging. Bypass grafting diffusely diseased vessels typically requires the use of innovative operations such as on-lay patches, endarterectomies and more than one graft for a single vessel. Patients with "full metal jackets" (or multiple stents) are typically not referred to cardiac surgeons and often end up as no-option patients despite the attempts of using these innovative surgeries.

In recent decades, the spectrum of patients referred for CABG are older and are afflicted with other morbidities such as hypertension, diabetes mellitus, cerebral and peripheral vascular disease, renal dysfunction, and chronic pulmonary disease. In addition, many patients referred for CABG have advanced diffuse CAD and have previously undergone at least one catheter-based intervention or surgical revascularization procedure that either failed or was not effective. Because of this, the patient's vessels may no longer be graftable and complete revascularization using conventional CABG may not be feasible. An incomplete myocardial revascularization procedure has been shown to adversely affect short-term and long-term outcomes after coronary surgery.

Due in part to some of the aforementioned reasons, reoperative CABG surgery is now commonplace, accounting for over twenty percent (20%) of cases in some clinics. It is well established that mortality for reoperative CABG operations is significantly higher than primary operations. As such, the risk profile of reoperative patients is significantly increased and such patients are subjected to an increased risk of both in-hospital and long-term adverse outcomes.

Further, clinicians have also turned to unconventional therapies to treat non-option patients. For example, coronary endarterectomy ("CE") has been used as an adjunct to CABG in a select group of patients with diffuse CAD in order to afford complete revascularization. However, while CE was first described in 1957 as a method of treating CAD without using cardiopulmonary bypass and CABG, this procedure has been associated with high postoperative morbidity and mortality rates and has been afforded much scrutiny. Nevertheless, CE is the only therapeutic option available for many no-option patients with diffuse CAD.

Similarly, because conventional therapies have proven ineffective or are unavailable to high risk patients, perioperative transmyocardial revascularization ("TMR") has been indicated for patients suffering from medically refractory angina. TMR has proven effective for most patients suffering from refractory angina; the mortality rate after TMR in patients with stable angina ranges between about one to twenty percent (1-20%). Furthermore, in one study, TMR resulted in a higher perioperatively mortality rate in patients with unstable angina than those with stable angina (27% versus 1%). Some even report an operative mortality rate as low as twelve percent (12%). Patients who experience angina and who cannot be weaned from intravenous nitroglycerin and heparin have a significantly higher operative mortality rate (16-27% versus 1-3%). Based on these findings, the clinical practice has been to avoid taking such patients to the operating room for TMR if at all possible. The success of TMR is thought to be due to improved regional blood flow to ischemic myocardium, but the precise mechanisms of its effects remain unclear.

D. Acute Applications

When a coronary artery becomes blocked, the flow of blood to the myocardium stops and the muscle is damaged. This process is known as myocardial infarction (MI). An MI can damage the myocardium, resulting in a scarred area that does not function properly. MI has an annual incidence rate of 1.5 million in the US and is the primary driver of roughly 500,000 cases of mortality and high morbidity rates in CAD patients. Immediate reperfusion of the myocardium following MI is clinically desirable to preserve as much heart tissue as possible. Current revascularization options include thrombolytic medications, percutaneous coronary intervention (PCI), or coronary artery bypass graft (CABG). While thrombolytic compounds can be administered swiftly in an acute care facility, the vast majority of MI patients require a PCI or CABG to adequately restore reliable blood flow to the heart tissue. Both of these revascularization techniques are clinically safe and effective, however, they require specialized staff and facilities, which are not available at all acute care facilities, or not available soon enough to preserve enough myocardial tissue in the wake of an MI. A significant effort has been undertaken in recent years to speed MI patients to the cath lab for PCI upon presenting, but these programs are not available everywhere, and even where available, do not often meet the 90 minute target of door to balloon time.

In the US, nearly 75,000 CAD patients annually present with atherosclerosis of the left main coronary artery (LMCA). The LMCA delivers oxygenated blood to 75% or more of the myocardium. An untreated, diseased LMCA results in 20% 1-year and 50% 7- to 10-year mortality rates. Historically, PCI of the LMCA (LMPCI) has been deemed too risky, however, recent advances in technique and tools have begun to allow an expanded LMCA patient population for PCI, especially in certain patient conditions where PCI is preferable to CABG (e.g., patients who are aging, delicate, and/or in critical condition).

The risks of LMPCI include prolonged myocardial ischemia from balloon inflations, "no-reflow phenomenon" (2-5% incidence rate), or coronary artery dissections (30% incidence rate). Existing circulatory support devices used to address these hemodynamic issues, such as the intra-aortic balloon pump (IABP) and left ventricle circulatory support devices (e.g., Impella 2.5), are unable to sufficiently meet the myocardium oxygen demands even though cardiac pumping mechanics are improved. The assistance from these devices is limited further during no-reflow and coronary artery dissection events. In addition, the clinically superior left ventricle circulatory support devices are complicated to use and require dedicated training and facilities, which has prevented widespread clinical adoption.

There are over 35,000 cardiogenic shock (CS) patients each year in the US. This condition severely complicates an MI event with in-hospital mortality rates exceeding 50 percent. PCI is the standard of care for these acute patients; however, the CS patient must be stabilized prior to intervention, according to ACC/AHA guidelines, using a short-term circulatory support device as a bridge. An IABP or left ventricle circulatory support device (e.g. Impella 2.5) can currently be utilized in these cases to stabilize the heart while awaiting revascularization.

The 200,000 S-T segment elevated MI (STEMI) patients per year in the US require immediate reperfusion of the myocardium. Thrombolytic medications are administered as the primary revascularization technique, however, 70 percent of those receiving thrombolysis fail to respond. Furthermore, 10 percent of those that initially respond to thrombolysis experience reocclusion while still an in-patient. These STEMI patients require clinically superior rescue PCI, as opposed to repeated thrombolysis.

Because only 1,200 out of 5,000 acute care hospitals are capable of performing PCI (and even fewer are capable of CABG), nearly 60 percent of STEMI patients do not achieve the required 90 minute time-frame for revascularization.

While awaiting revascularization, IAPB currently is the preferred circulatory assist device and is indicated for use by critical care unit (CCU), intensive care unit (ICU) and emergency medicine (ER) physicians in a variety of clinical settings. However, the IABP's use in MI events remains at less than 5 percent of cases due to complicated training and device-related malfunctions in 12-30% of all cases.

Circulatory support devices used in these cases have two major problems: inability to adequately augment blood flow in flow-limiting atherosclerotic coronary arteries to a damaged myocardium, and 12-30% device complication incidence rates, including peripheral ischemic, compartment syndrome, infection, hematological issues, and mechanical issues.

BRIEF SUMMARY

In at least one embodiment of a method of organ perfusion of the present disclosure, the method comprises the steps of positioning at least part of a first catheter having a cannula within an artery of a patient, the first catheter configured to permit arterial blood to flow therethrough and further configured to permit a portion of the arterial blood to flow through the cannula, positioning at least part of a second catheter within a vein of the patient at or near a target organ, the second catheter configured to receive some or all of the portion of the arterial blood, and connecting the cannula of the first catheter to a portion of the second catheter so that some or all of the portion of the arterial blood flowing through the cannula is provided into the vein to treat a condition or disease of the target organ. In another embodiment, the step of positioning at least part of the first catheter is performed by positioning at least part of the first catheter within an artery selected from the group consisting of a femoral artery, an internal femoral artery, and an iliac artery. In yet another embodiment, the step of positioning at least part of the second catheter is performed by positioning at least part of the second catheter within a vein selected from the group consisting of a distal saphenous vein and a deep muscle vein. In an additional embodiment, the step of connecting the cannula to the portion of the second catheter is performed to permit blood flow from the cannula to the vein to treat a diabetic condition.

In at least one embodiment of a method of organ perfusion of the present disclosure, the step of positioning at least part of the first catheter is performed by positioning at least part of the first catheter within an artery selected from the group consisting of a femoral artery, an internal femoral artery, an iliac artery, an axillary artery, a brachial artery, and a subclavian artery. In an additional embodiment, the step of positioning at least part of the second catheter is performed by positioning at least part of the second catheter within a renal vein. In yet an additional embodiment, the step of connecting the cannula to the portion of the second catheter is performed to permit blood flow from the cannula to the vein to treat a kidney condition.

In at least one embodiment of a method of organ perfusion of the present disclosure, the step of positioning at least part of the first catheter is performed by positioning at least part of the first catheter within an artery selected from the group consisting of a femoral artery, an internal femoral artery, an iliac artery, an axillary artery, a brachial artery, and an epigastric artery. In another embodiment, the step of positioning at least part of the second catheter is performed by positioning at least part of the second catheter within a mesenteric vein. In yet another embodiment, the step of connecting the cannula to the portion of the second catheter is performed to permit blood flow from the cannula to the vein to treat an intestinal condition.

In at least one embodiment of a method of organ perfusion of the present disclosure, the step of positioning at least part of the first catheter is performed by positioning at least part of the first catheter within an artery selected from the group consisting of an external carotid artery, a brachial artery, and an axillary artery. In an additional embodiment, the step of positioning at least part of the second catheter is performed by positioning at least part of the second catheter within a jugular vein. In yet an additional embodiment, the step of connecting the cannula to the portion of the second catheter is performed to permit blood flow from the cannula to the vein to treat a spinal condition.

In at least one embodiment of a method of organ perfusion of the present disclosure, the step of positioning at least part of the first catheter is performed by positioning at least part of the first catheter within an epigastric artery. In another embodiment, the step of positioning at least part of the second catheter is performed by positioning at least part of the second catheter within a penile dorsal vein. In yet another embodiment, the step of connecting the cannula to the portion of the second catheter is performed to permit blood flow from the cannula to the vein to treat a penile condition.

In at least one embodiment of a method of organ perfusion of the present disclosure, the method comprises the steps of positioning at least a portion of an arterial tube of a perfusion system within an artery of a patient, the arterial tube configured to permit arterial blood to flow therethrough, positioning at least a portion of a first catheter of the perfusion system into a vein of the patient at or near a target organ, the first catheter configured to receive some or all of the arterial blood from the arterial tube, and operating a first flow regulator of the perfusion system so that some or all of the arterial blood flowing through the arterial tube is provided into the vein to treat a condition or disease of the target organ. In another embodiment, the step of positioning at least part of the arterial tube is performed by positioning at least part of the arterial tube within an artery selected from the group consisting of a femoral artery, an internal femoral artery, and an iliac artery. In yet another embodiment, the step of positioning at least part of the first catheter is performed by positioning at least part of the first catheter within a vein selected from the group consisting of a distal saphenous vein and a deep muscle vein. In an additional embodiment, the step of operating a first flow regulator is performed to permit blood flow from the arterial tube to the vein to treat a diabetic condition.

In at least one embodiment of a method of organ perfusion of the present disclosure, the step of positioning at least part of the arterial tube is performed by positioning at least part of the arterial tube within an artery selected from the group consisting of a femoral artery, an internal femoral artery, an iliac artery, an axillary artery, a brachial artery, and a subclavian artery. In an additional embodiment, the step of positioning at least part of the first catheter is performed by positioning at least part of the first catheter within a renal vein. In yet an additional embodiment, the step of operating a first flow regulator is performed to permit blood flow from the cannula to the vein to treat a kidney condition.

In at least one embodiment of a method of organ perfusion of the present disclosure, the step of positioning at least part of the arterial tube is performed by positioning at least part of the arterial tube within an artery selected from the group consisting of a femoral artery, an internal femoral artery, an iliac artery, an axillary artery, a brachial artery, and an epigastric artery. In another embodiment, the step of positioning at least part of the first catheter is performed by positioning at least part of the first catheter within a mesenteric vein. In yet another embodiment, the step of operating a first flow regulator is performed to permit blood flow from the cannula to the vein to treat an intestinal condition.

In at least one embodiment of a method of organ perfusion of the present disclosure, the step of positioning at least part of the arterial tube is performed by positioning at least part of the arterial tube within an artery selected from the group consisting of an external carotid artery, a brachial artery, and an axillary artery. In an additional embodiment, the step of positioning at least part of the first catheter is performed by positioning at least part of the first catheter within a jugular vein. In yet an additional embodiment, the step of operating a first flow regulator is performed to permit blood flow from the cannula to the vein to treat a spinal condition.

In at least one embodiment of a method of organ perfusion of the present disclosure, the step of positioning at least part of the arterial tube is performed by positioning at least part of the arterial tube within an epigastric artery. In another embodiment, the step of positioning at least part of the first catheter is performed by positioning at least part of the first catheter within a penile dorsal vein. In yet another embodiment, the step of operating a first flow regulator is performed to permit blood flow from the cannula to the vein to treat a penile condition.

In at least one embodiment of a method of organ perfusion of the present disclosure, the step of positioning at least a portion of a first catheter further comprises the step of inflating an expandable balloon positioned along the portion of the first catheter positioned in the vein to secure the portion of the first catheter within the vein. In an additional embodiment, the step of positioning at least a portion of an arterial tube further comprises the step of operating the first flow regulator to regulate blood flow from the artery to the vein prior to the step of positioning at least a portion of a first catheter so to substantially eliminate an introduction of a gas within at least a portion of the perfusion system to the vein. In yet an additional embodiment, the method further comprises the step of removing the at least a portion of a first catheter from the vein within about 24 hours after positioning the at least a portion of a first catheter into the vein. In another embodiment, the method further comprises the step of removing the at least a portion of a first catheter from the vein between about 24 hours and about 48 hours after positioning of the at least a portion of a first catheter into the vein. In yet another embodiment, the method further comprises the step of removing the at least a portion of a first catheter from the vein after about 48 hours after positioning of the at least a portion of a first catheter into the vein. In at least one embodiment of a method of organ perfusion of the present disclosure, the step of operating a first flow regulator of the perfusion system is performed to control blood pressure to limit potential injury to the vein of the patient. In another embodiment, the step of positioning at least a portion of a first catheter is performed to position the first catheter at a location so not to impede coronary venous return. In yet another embodiment, the method further comprises the step of temporarily deflating the expandable balloon during operation of the system to alleviate a localized increase in pressure or edema at or near the expandable balloon.

BRIEF DESCRIPTION OF THE DRAWINGS

FIG. 2A shows a side view of the catheter of FIG. 1 in a collapsed position, according to at least one embodiment of the present disclosure;

FIG. 2B shows a side view of the catheter of FIG. 1 in an extended position, according to at least one embodiment of the present disclosure;

FIG. 8A shows a side view of the catheter of FIG. 1 in a collapsed position within an introducer, according to at least one embodiment of the present disclosure;

FIG. 8B, shows a side view of the catheter of FIG. 1 being introduced via an introducer into an arterial vessel, according to at least one embodiment of the present disclosure;

DETAILED DESCRIPTION

Figure 1:
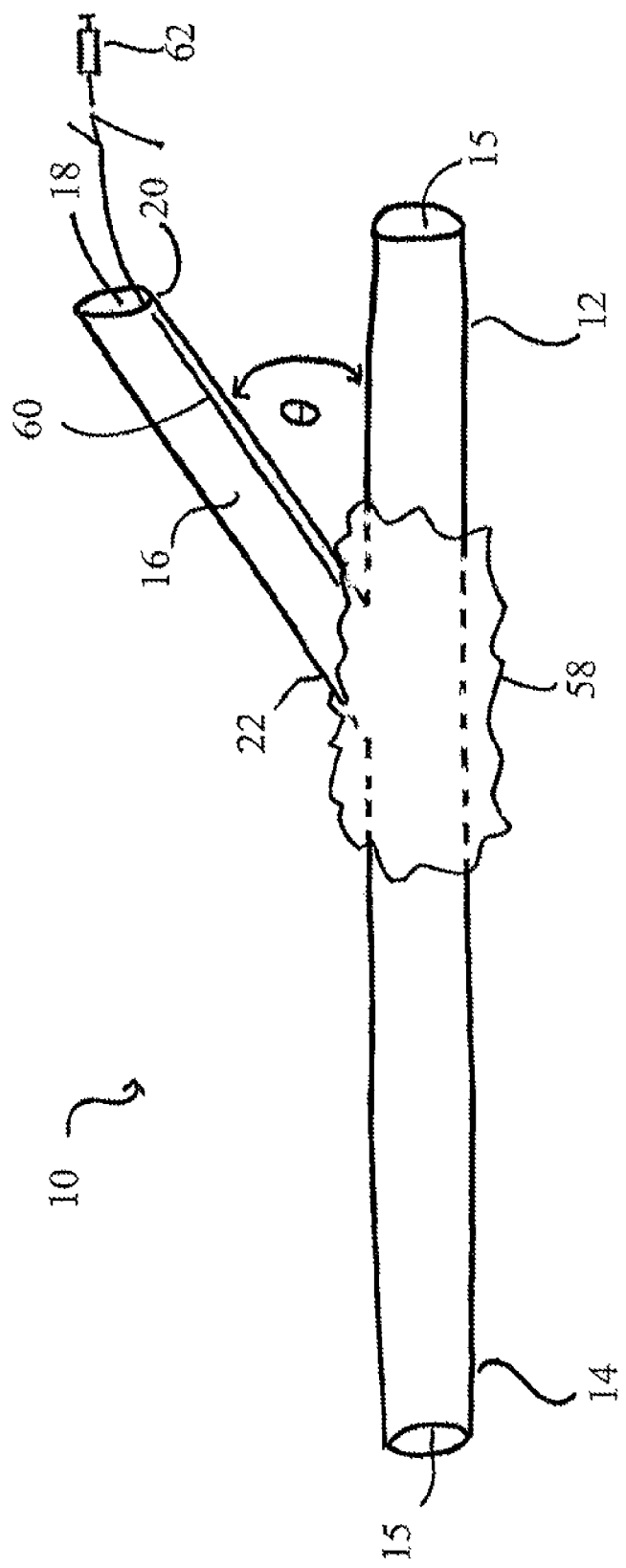
FIG. 1 shows a side view of a catheter for placement within an arterial vessel and that may be used to deliver retroperfusion therapy, according to at least one embodiment of the present disclosure.

The embodiments discussed herein include devices, systems, and methods useful for providing selective autoretroperfusion to the venous system. In addition, and with various embodiments of devices and systems of the present disclosure, said devices and/or systems can also be used to achieve a controlled arterialization of the venous system. For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The devices, systems and methods disclosed herein can be used to safely and selectively arterialize venous vessels in order to decrease the stress thereon and prevent rupture of the same. Accordingly, through the use of the devices, systems and methods disclosed herein, long-term autoretroperfusion of oxygenated blood through the coronary venous system can be achieved, thereby providing a continuous supply of oxygen-rich blood to an ischemic area of a tissue or organ. While the devices, systems and methods disclosed herein are described in connection with a heart, it will be understood that such devices, systems and methods are not limited in their application solely to the heart and the same may be used in connection with any ischemic tissue and/or organ in need of an oxygen-rich blood supply.

Selective auto-retroperfusion (SARP) can be indicated for both chronic and acute applications, and exemplary catheters 10 and/or systems 100 of the present disclosure (and as referenced in further detail herein) can be used in connection therewith. References to "acute" for SARP applications are used generally to indicate the amount of time that an exemplary catheter 10 and/or system 100 of the present disclosure may be in use on a given patient. In at least one embodiment, catheter 10 and/or system 100, or portions thereof, will be sterile and intended for disposal after a single use. In at least one embodiment of a system 100 useful in connection with an acute indication, use of system 100 could be limited to less than 24 hrs.

Now referring to FIG. 1, a side view of a catheter 10 is shown. The catheter 10 is configured to be placed within an arterial vessel and comprises a flexible, elongated tube having a proximal end 12, a distal end 14 and at least one lumen 15 extending between the proximal end 12 and the distal end 14. The dimensions of the catheter 10 may vary depending on the particulars of a specific patient or with respect to the artery to be cannulated. For example and without limitation, where the catheter 10 is used to in a system for autoretroperfusion of the coronary sinus, the catheter 10 may comprise a diameter of about 2.7 millimeters to about 4 millimeters (about 8 Fr to about 12 Fr). Furthermore, the at least one lumen 15 of the catheter 10 comprises a sufficient diameter such that blood can flow therethrough in addition, the catheter 10 may be comprised of any appropriate material, including without limitation, polyurethane or silicone rubber. Furthermore, the catheter 10 may be coated with heparin or any other suitable anti-coagulant such that the catheter 10 may be placed within a vessel for an extended period of time without inhibiting blood flow due to coagulation.

The distal end 14 of the catheter 10 is configured to allow arterial blood to flow therethrough and into the at least one lumen 15 of the catheter 10. Similarly, the proximal end 12 of the catheter 10 is configured to allow blood within the at least one lumen 15 to flow out of the catheter 10. Accordingly, when the catheter 10 is positioned within an arterial vessel, the oxygenated blood is allowed to flow into the catheter 10 through the distal end 14 of the catheter 10, through the at least one lumen 15, and out of the catheter 10 through the proximal end 12 of the catheter 10. In this manner, placement of the catheter 10 within a vessel does not inhibit the flow of blood through the vessel or significantly affect the pressure of the blood flow within the vessel.

As shown in FIG. 1, the catheter 10 further comprises a projection cannula 16 that extends from the proximal end 12 of the catheter 10 and forms a Y-shaped configuration therewith. The projection cannula 16 comprises a flexible tube of material that is appropriate for insertion within a vessel and placement within an opening in a vessel wall. Furthermore, the projection cannula 16 comprises at least one lumen 18, a proximal end 20, and a distal end 22. The distal end 22 of the projection cannula 16 is coupled with the body of the catheter 10 and configured to allow the lumen 18 of the projection cannula 16 to communicate with at least one of the at least one lumens 15 of the catheter 10. Accordingly, when blood flows through the at least one lumen of the catheter 10, a portion of the blood flow enters the lumen 18 of the projection cannula 16 through the distal end 22 thereof and flows out through the proximal end 20 of the projection cannula 16. In this manner, the catheter 10 is capable of bifurcating the flow of blood through the vessel in which it is inserted and routing some of that blood flow out of the vessel and to another location.

This bifurcation can be exploited to modify the pressure of the blood flowing through the projection cannula 16 and/or through the proximal end 12 of the catheter 10 by manipulating the dimensions of the projection cannula 16 and the body of the catheter 10. For example, and without limitation, if the diameter of the projection cannula 16 is less than the diameter of the at least one lumen 15 of the catheter 10; the majority of the blood will flow through the proximal end 12 of the catheter 10 and the pressure of the remaining blood that flows through the smaller projection cannula 16 will necessarily be reduced. Predictably, the smaller the diameter of the lumen 18 of the projection cannula 16, the greater the pressure drop that can be achieved in the blood flowing through the lumen 18 of the projection cannula 16. Accordingly, with respect to the catheter's 10 application to autoretroperfusion therapies, the projection cannula 16 can be used to re-route blood flow from an artery to a vein while simultaneously achieving the necessary pressure drop in the re-routed blood between the arterial system and unarterialized venous system. Moreover, the catheter 10 is capable of maintaining substantially normal blood flow through the artery in which it is housed as the arterial blood not re-routed through the projection cannula 16 is allowed to flow through the open proximal end 12 of the catheter 10 and back into the artery in the normal antegrade fashion.

Due to the configuration of the projection cannula 16 and the material of which it is comprised, the projection cannula 16 is capable of hingedly moving relative to the body of the catheter 10 between a collapsed position and an extended position. Now referring to FIGS. 2A and 2B, the projection cannula 16 is shown in the collapsed position (FIG. 2A) and in the extended position (FIG. 2B). When the projection cannula 16 is in the collapsed position, the projection cannula 16 is positioned substantially parallel with the body of the catheter 10. Alternatively, when the projection cannula 16 is in the extended position, the projection cannula 16 is positioned such that the projection cannula 16 forms an angle θ with the proximal end 12 of the catheter 10. The value of angle θ may be selected depending on the desired application of the catheter 10. For example, in at least one embodiment, the angle θ may comprise any value ranging between about 15° and about 90°. In another example, the angle θ may comprise about 45° when the projection cannula 16 is in the extended position.

The projection cannula 16 is biased such that, when it is not subject to a downward force, the projection cannula 16 rests in the expanded position. Conversely, when a downward force is applied to the projection cannula 16 by way of an introducer or otherwise, the projection cannula 16 moves into and remains in the collapsed position until the downward force is removed. In this manner, the projection cannula 16 may be introduced into a vessel in the collapsed position through the use of an introducer or shaft and thereafter move into the expanded position when the catheter 10 is properly positioned within the vessel and the introducer or shaft is removed.

Optionally, as shown in FIG. 1, the catheter 10 may further comprise an expandable balloon 58 coupled with an intermediary portion of the external surface of the catheter 10 such that the expandable balloon 58 encases the catheter 10 and the distal end 22 of the projection cannula 18. The expandable balloon 58 may be any expandable balloon 58 that is appropriate for insertion within a vessel and may comprise any material suitable for this function, including without limitation, polyethylene, latex, polyestherurethane, polyurethane, sylastic, silicone rubber, or combinations thereof. In operation, the expandable balloon 58 can be used to anchor the catheter 10 in a desired position within a vessel wall and prevent leakage from the opening in the vessel wall through which the projection cannula 16 traverses.

The expandable balloon 58 is capable of being controlled by a clinician such that it can inflate and/or deflate to the proper size. The sizing of the expandable balloon 58 will differ between patients and applications. The expandable balloon 58 may be in fluid communication with a balloon inflation port 62 through a secondary lumen 60 within the lumen 18 of the projection cannula 16. Alternatively, the expandable balloon 58 may be in fluid communication with the balloon inflation port 62 through a tube or other means that is positioned within the lumen 18 of the projection cannula 16 as shown in FIG. 1. The balloon port 62 may be positioned subcutaneously or otherwise such that a clinician can easily access the balloon port 62 when the catheter 10 is positioned within a vessel. In this manner the balloon port 62 can be accessed by a clinician, subcutaneously, percutaneously or otherwise, and used to inflate or deflate the expandable balloon 58 with no or minimal invasion to the patient.

Figure 3:
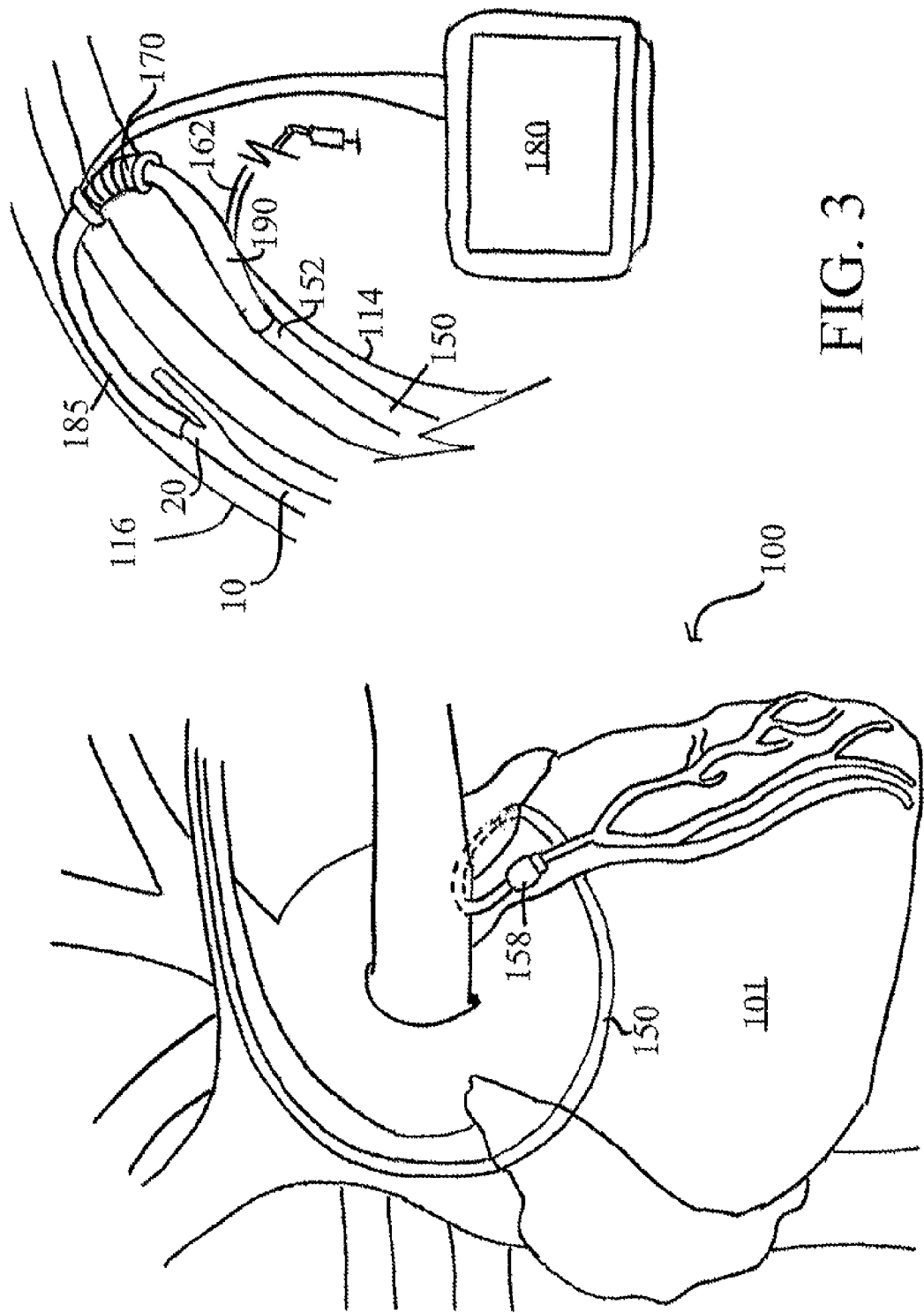
FIG. 3 shows a side view of an autoretroperfusion system positioned to deliver retroperfusion therapy to a heart, according to at least one embodiment of the present disclosure.

Now referring to FIG. 3, an autoretroperfusion system 100 is shown positioned to allow arterial blood to irrigate the coronary sinus of a heart 101. With respect to the heart 101, the autoretroperfusion system 100 may be used for treatment of myocardial infarctions by injecting arterial blood into the coronary sinus in synchronism with the patient's heartbeat. Furthermore, the autoretroperfusion system 100 is capable of controlling the pressure of the arterial blood flow as it enters the venous vessel such that when the arterial blood flow is first introduced into the venous system, the pressure of the re-routed arterial blood flow is reduced to protect the thinner venous vessels. In this manner, the venous system is allowed to gradually arterialize. Further, after the selected venous vessel has sufficiently arterialized, the autoretroperfusion system 100 is capable of reducing or ceasing its influence on the pressure of the re-routed arterial blood flow such that the standard arterial blood flow pressure is thereafter allowed to flow into the arterialized venous vessel.

Autoretroperfusion system 100 comprises the catheter 10, a second catheter 150, and a connector 170. The catheter 10 is for placement within an arterial vessel and is configured as previously described in connection with FIGS. 1-2B. The second catheter 150 is configured for placement within the venous system. The connector 170 is configured to form an anastomosis between the catheter 10 and the second catheter 150 and further functions to monitor various data points on the blood flow flowing therethrough. In addition, in at least one embodiment, the connector 170 is capable of controlling the pressure of arterial blood flowing therethrough.

The second catheter 150 is configured for placement within a venous vessel wall 114 and comprises a flexible tube having a proximal end 152, a distal end 154 and at least one lumen 156 extending between the proximal end 152 and the distal end 154. Both the proximal end 152 and the distal end 154 of the second catheter 150 are open and in communication with the at least one lumen 156 of the second catheter 150, thereby allowing blood to flow into the at least one lumen 156 through the proximal end 152 and out of the distal end 154 back into the venous vessel 114. The second catheter 150 may be any catheter known in the art that is capable of intravascular insertion and advancement through the venous system and may comprise any appropriate material, including without limitation, polyurethane or silicone rubber. In at least one embodiment, the second catheter 150 is configured to receive a guidewire 510 (see FIGS. 4A and 4B) through the at least one lumen 156 to facilitate the intravascular delivery of the distal end 154 of the second catheter 150 into the desired location of the venous vessel 114. Furthermore, similar to the catheter 10, the second catheter 150 may be coated with heparin or any other suitable anti-coagulant prior to insertion in order to facilitate the extended placement of the second catheter 150 within the venous vessel 114. Accordingly, the autoretroperfusion system 100 may be used to deliver chronic retroperfusion treatment to an ischemic area of a body.

Figure 4:
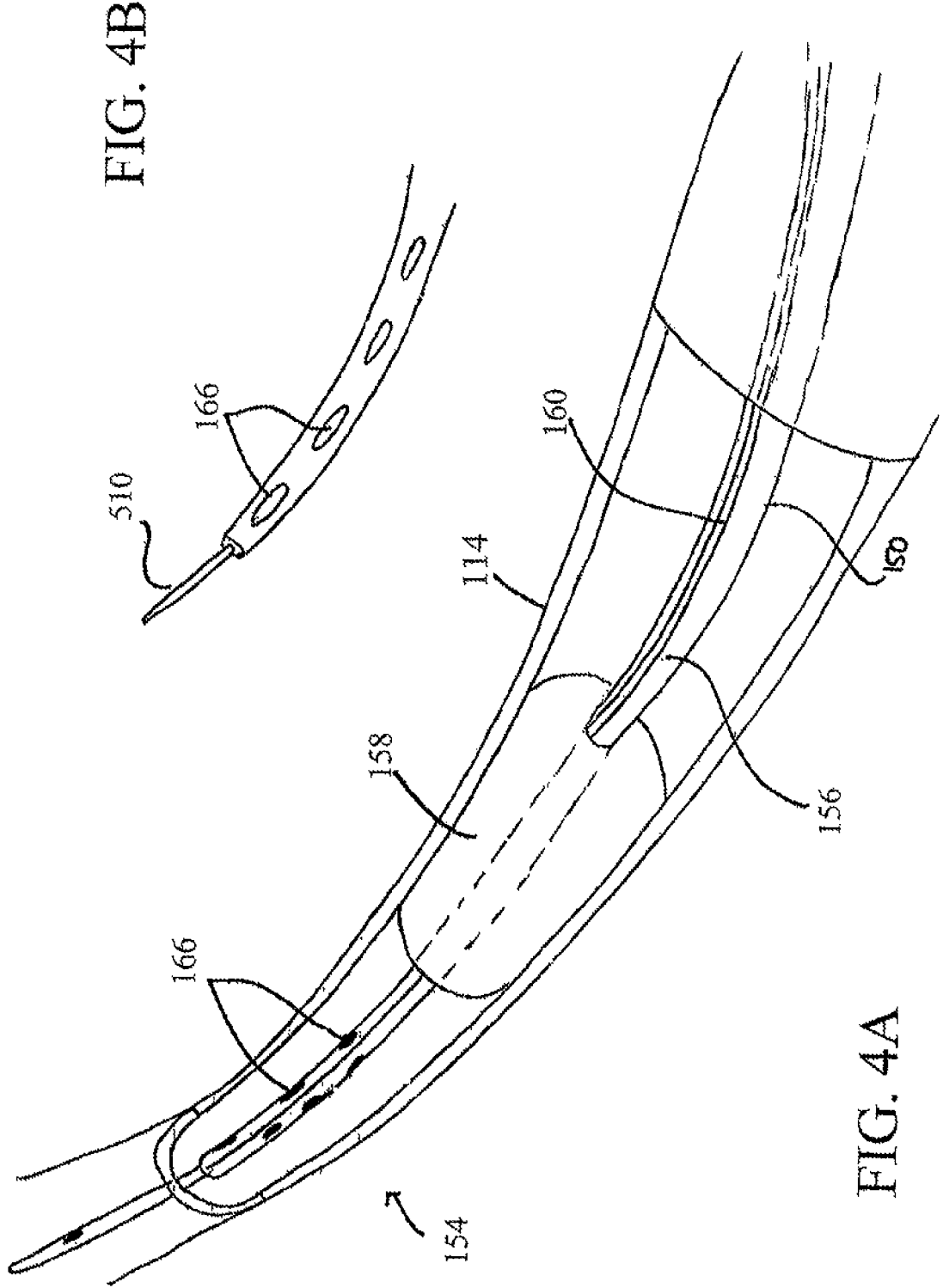
FIGS. 4A and 4B show perspective views of the distal end of a venous catheter used in the autoretroperfusion system of FIG. 3, according to at least one embodiment of the present disclosure.

FIGS. 4A and 4B show side views of the distal end 154 of the second catheter 150 positioned within the venous vessel wall 114. As shown in FIG. 4A, the distal end 154 of the second catheter 150 may further comprise an expandable balloon 158 coupled with the external surface of the second catheter 150. In operation, the expandable balloon 158 can be used to anchor the distal end 154 of the second catheter 150 in the desired location within the venous vessel wall 114. The expandable balloon 158 may be any expandable balloon that is appropriate for insertion within a vessel and can be formed of any material suitable for this function, including without limitation, polyethylene, latex, polyestherurethane, polyurethane, sylastic, silicone rubber, or combinations thereof.

The expandable balloon 158 is capable of being controlled by a clinician such that it can inflate and/or deflate to the proper size. The sizing of the expandable balloon 158 will differ between patients and applications and it is often important to determine the proper sizing of the expandable balloon 158 to ensure the distal end 154 of the second catheter 150 is securely anchored within the desired location of the vessel wall 114. The accurate size of the expandable balloon 158 can be determined through any technique known in the art, including without limitation, by measuring the compliance of the expandable balloon 158 ex vivo or in vivo. In addition, the distal end 154 of the second catheter 150 may further comprise a plurality of electrodes that are capable of accurately measuring the cross-sectional area of the vessel of interest as is known in the art. For example, the plurality of electrodes may comprise a combination of excitation and detection electrodes as described in detail in the currently pending U.S. patent application Ser. No. 11/891,981 entitled System and Method for Measuring Cross-Sectional Areas and Pressure Gradients in Luminal Organs, and filed on Aug. 14, 2007, which is hereby incorporated by reference in its entirety. In at least one embodiment, such electrodes may comprise impedence and conductance electrodes and may be used in connection with ports for the suction of fluid from the vessel and/or the infusion of fluid therein.

The expandable balloon 158 may be in fluid communication with a secondary lumen 160 disposed within the at least one lumen 156 of the second catheter 150. In this example, the secondary lumen 160 is coupled with a balloon port 162 that extends from the proximal end 152 of the second catheter 150 (see FIG. 3). Accordingly, when the autoretroperfusion system 100 is positioned within a patient, the balloon port 162 can be easily accessed by a clinician, subcutaneously, percutaneously or otherwise, and used to inflate or deflate the expandable balloon 158 with no or minimal invasion to the patient.

As shown in FIGS. 4A and 4B, the distal end 154 of the second catheter 150 may further comprise at least one sensor 166 coupled therewith. In at least one embodiment, the at least one sensor 166 is disposed on the distal end 154 of the second catheter 150 distally of the expandable balloon 158; however, it will be understood that the at least one sensor 166 may be disposed in any location on the distal end 154 of the second catheter 150.

The at least one sensor 166 may be used for monitoring purposes and, for example, may be capable of periodically or continuously monitoring the pressure of the blood flow flowing through the at least one lumen 156 of the first catheter 150 or the venous vessel 14 in which the second catheter 150 is inserted. Additionally, one of the at least one sensors 166 may be used to monitor the pH or the concentrations of carbon dioxide, lactate, or cardiac enzymes within the blood. Furthermore, the at least one sensor 166 is capable of wirelessly communicating the information it has gathered to a remote module through the use of telemetry technology, the internet, or other wireless means, such that the information can be easily accessed by a clinician on a real-time basis or otherwise.

Now referring back to FIG. 3, the autoretroperfusion system 100 further comprises a connector 170. The connector 170 comprises any connector or quick connector known in the medical arts that is capable of forming an anastomosis between an artery and a vein such that oxygenated blood from the arterial system can flow into the venous system. For example, the connector 170 may comprise an annular connector that is capable of coupling with the proximal end 20 of the projection cannula 16 of the catheter 10 and with the proximal end 152 of the second catheter 150 such that arterial blood can flow continuously from the at least one lumen 15 of the catheter 10 to the at least one lumen 156 of the second catheter 150. The connector 170 may be formed of any suitable material known in the art including, but not limited to, silicon rubber, poly(tetrafluoroethene), and/or polyurethane.

The connector 170 of the autoretroperfusion system 100 may comprise a pressure/flow regulator unit that is capable of measuring the flow rate of the blood moving therethrough, the pressure of the blood moving therethrough, and/or other data regarding the blood flowing through the anastomosis. The connector 170 may also be capable of transmitting such gathered data to a remote module 180 through a lead placed intravascularly or, in the alternative, through telemetry or another wireless means. The remote module 180 may comprise any device capable of receiving the data collected by the connector 170 and displaying the same. For example, and without limitation, the remote module 180 may comprise any display device known in the art or a computer, a microprocessor, hand-held computing device or other processing means.

Additionally, the connector 170 may further comprise a means for regulating the blood flow through the anastomosis. One of the main challenges of successfully delivering retroperfusion therapies is that the arterial blood pressure must be reduced prior to being introduced into a vein due to the thinner and more fragile anatomy of venous walls. Indeed, subjecting a non-arterialized venous vessel to the high pressures of arterial blood flow typically results in rupture of the venous vessel. Accordingly, with retroperfusion therapies, it is critical to ensure that the pressure of the arterial blood flow is at least initially controlled such that the venous vessel can arterialize prior to being subjected to the unregulated pressure of the arterial blood flow.

In at least one embodiment the connector 170 may comprise an external compression device to facilitate the control of the flow rate of the blood moving through the anastomosis. Alternatively, other means that are known in the art may be employed to regulate the blood flow and pressure of the blood flowing through the anastomosis formed by the connector 170. In at least one embodiment, the means for regulating the blood flow through the anastomosis formed by the connector 170 is capable of regulating the pressure and/or flow velocity of the blood flowing through the anastomosis. For example, the means for regulating blood flow can be adjusted to ensure that about a 50 mg Hg pressure drop occurs in the blood flow between the arterial vessel and the venous vessel.

The connector 170 is capable of not only transmitting data to the remote module 180, but also receiving commands from the remote module 180 and adjusting the means for regulating blood flow pursuant to such commands. Accordingly, when the autoretroperfusion system 100 is positioned within a patient for retroperfusion therapy, a clinician can use the remote module 180 to view the blood flow data collected by the connector 170 and non-invasively adjust the connector 170 to achieve the desired pressure and/or flow through the anastomosis. Such remote control of the connector 170 is particularly useful as a clinician may incrementally decrease the connector's 170 regulation of the blood flow without surgical intervention during the venous arterialization process and/or after the venous vessel arterializes.

Further, where the remote module 180 comprises a computer or other processing means, the remote module 180 is also capable of being programmed to automatically analyze the data received from the connector 170 and, based on the results thereof, suggest how to adjust the means of regulating the blood flow of the connector 170 and/or automatically adjust the means of regulating the blood flow of the connector 170 to achieve the optimal result. For example, and without limitation, when the autoretroperfusion system 100 is implanted into a patient and the anastomosis is first performed, the remote module 180 can automatically adjust the means for regulating the blood flow of the connector 170 based on the initial blood flow data received by the remote module 180. In this manner, the desired pressure drop between the arterial system and the venous system is immediately achieved and the risk of venous rupture is significantly reduced.

Alternatively, where the connector 170 of the autoretroperfusion system 100 does not comprise a means for regulating blood flow, the gradual arterialization of the venous vessel can be achieved through other techniques known in the art. For example, in at least one embodiment, the autoretroperfusion system 100 further comprises a coil designed to at least partially occlude the vein of interest. In this manner, the pressure is allowed to build in front of the portion of the vein at least partially occluded by the coil and the vein gradually arterializes. In this at least one embodiment, the coil may comprise a metallic memory coil (made of nitinol, stainless steel or other acceptable materials that are radiopaque) and is covered with polytetrafluorethylene, polyethylene terephthalate, polyurethane or any other protective covering available in the medical arts.

Additionally, gradual arterialization can be performed by the second catheter 150. In this embodiment of autoretroperfusion system 100, the at least one lumen 156 of the second catheter 150 is designed to provide an optimal stenosis geometry to facilitate the desired pressure drop as the arterial blood flows therethrough and into the venous system. For example, and without limitation, the at least one lumen 156 may further comprise an internal balloon or resorbable stenosis as disclosed in International Patent Application No. PCT/US2006/029223, entitled "Devices and Methods for Controlling Blood Perfusion Pressure Using a Retrograde Cannula," filed Jul. 28, 2006, which is hereby incorporated by reference herein.

In at least one embodiment, the stenosis comprises an internal expandable balloon (not shown) positioned within the lumen 156 of the second catheter 150. In this at least one embodiment, the internal expandable balloon can be used to provide a pressure drop between the arterial and venous systems as is required to achieve the gradual arterialization of the target vein. The internal expandable balloon and the external expandable balloon 158 of the second catheter 150 may positioned concentrically or, alternatively, the internal expandable balloon and the expandable balloon 158 may be coupled with distinct portions of the second catheter 150.

The internal expandable balloon may comprise any material suitable in the medical arts, including, without limitation, polyethylene, latex, polyestherurethane, polyurethane, sylastic, silicone rubber, or combinations thereof. Further, the internal expandable balloon may be in fluid communication with a tertiary lumen (not shown) disposed within the at least one lumen 156 or the second catheter 150. In this embodiment, the tertiary lumen is also in fluid communication with an internal balloon port that extends from the proximal end 152 of the second catheter 150. Accordingly, the internal balloon port can be easily accessed by a clinician, subcutaneously, percutaneously or otherwise, and the internal balloon port can be used to inflate or deflate the internal expandable balloon with minimal or no discomfort to the patient when the system 100 is in operation. Alternatively, the internal expandable balloon may be in fluid communication with the at least one lumen 156 of the second catheter 150. In this example, the arterial blood flow through the at least one lumen 156 functions to inflate and deflate the internal expandable balloon in conjunction with the systolic and diastolic components of a heart beat.

The internal expandable balloon may be sized to a specific configuration in order to achieve the desired stenosis. In one embodiment, the size of the desired stenosis may be obtained by measuring the pressure at the tip of the distal end 156 of the second catheter 150 with the at least one sensor 166 while the internal expandable balloon is being inflated. Once the desired intermediate pressure is obtained, the internal expandable balloon volume may then be finalized and the vein is thereafter allowed to arterialize at the modified pressure for a defined period of time. At the end of the defined period (typically about 2-3 weeks), the internal expandable balloon may be removed from the at least one lumen 156 of the second catheter 150.

Insertion and/or removal of the internal expandable balloon from the system 100 may be achieved through the internal balloon port and the related tertiary lumen of the second catheter 150. For example, if the internal expandable balloon is no longer necessary to control the pressure on the venous system because the arterialization of the vein is substantially complete, the internal expandable balloon can be deflated through use of internal balloon port and withdrawn from the system 100 through the tertiary lumen and the internal balloon port.

Other embodiments of the system 100 may comprise other suitable means for providing a stenosis within the at least one lumen 156 of the second catheter 150 such that a pressure drop is achieved in blood flowing therethrough. For example, while a stenosis can be imposed by inflation of the internal expandable balloon, it may also be imposed through positioning a resorbable material within the at least one lumen 156 of the second catheter 150. The resorbable stenosis may be comprised of a variety of materials including, for example and without limitation, magnesium alloy and polyols such as mannitol, sorbitol and maltitol. The degradation rate of the resulting resorbable stenosis will be dependent, at least in part, upon on what type of material(s) is selected to make-up the resorbable stenosis and the same may be manipulated to achieve the desired effect.

In addition to the aforementioned components of the autoretroperfusion system 100, the autoretroperfusion system 100 may further include a first graft 185 and a second graft 190 as shown in FIG. 3. In this embodiment, the first graft 185 is coupled with the proximal end 20 of the projection cannula 16 (that extends through the exterior arterial wall 116) and the connector 170. Further, the second graft 190 is coupled with the proximal end 152 of the second catheter 150 (positioned within the venous vessel wall 114) and the connector 170. Accordingly, in this at least one embodiment, the second graft 190 is capable of traversing the venous vessel wall 114 in such a manner that the anastomosis is sealed and no blood flow is allowed to leak from the anastomosed vein 114.

In this manner, the first and second grafts 185, 190 facilitate the formation of an elongated anastomosis between the venous and arterial vessels 114, 116 and thereby relieve any pressure that may be applied to the two vessels 114, 116 due to the anastomosis formed therebetween. For example and without limitation, in at least one embodiment the combined length of the grafts 185, 190 and the connector 170 is about 6 centimeters. However, it will be understood that the grafts 185, 190 may comprise any length(s) so long as the dimensions allow for an anastomosis to form between the applicable vessels and a fully developed blood flow is achieved from the artery to the venous vessel of interest.

Alternatively, the autoretroperfusion system 100 may only comprise the second graft 190 in addition to the catheter 10, the second catheter 150 and the connector 170. In this embodiment, the connector 170 is coupled with the proximal end 20 of the projection cannula 16 and the second graft 190. Furthermore, the second graft 190 is further coupled with the proximal end 152 of the second catheter 150 such that the second graft 190 traverses an opening within the venous vessel wall 114 (see FIG. 5).

The grafts 185, 190 may comprise any biocompatible, non-resorbable material having the necessary strength to support the surrounding tissue and withstand the pressure asserted by the blood flow therethrough. Furthermore, the grafts 185, 190 must exhibit the necessary flexibility to form an anastomosis between the vein and the artery within which the catheter 10 and the second catheter 150 are respectively housed. For example, and without limitation, the grafts 185, 190 may comprise any conventional implant including synthetic and natural prosthesis, grafts, and the like. The grafts 185, 190 may also comprise a variety of suitable materials, including those conventionally used in anastomosis procedures, including, without limitation, natural and synthetic materials such as heterologous tissue, homologous tissue, polymeric materials, Dacron, fluoropolymers, and polyurethanes. For example, and without limitation, the first and second grafts 185, 190 may comprise a material such as GORE-TEX (polytetraflouroethylene). The grafts 185, 190 may be coated with heparin or any other suitable anti-coagulant. Accordingly, the first graft 185 and the second graft 190 may be placed within a vessel or have blood flow therethrough for an extended period of time without inhibiting blood flow due to coagulation.

In at least one embodiment of the autoretroperfusion system 100, the components of the system 100 are available in a package. Here, the package may also contain at least one sterile syringe containing the fluid to be injected into the balloon port 62 to inflate the expandable balloon 58 of the catheter 10 and/or the balloon port 162 to inflate the expandable balloon 158 of the second catheter 150. Furthermore, the package may also contain devices to facilitate delivery of the autoretroperfusion system 100 such as venous and arterial access devices, a delivery catheter, a guidewire and/or mandrel, an introducer to maintain the catheter 10 in the collapsed position during delivery and, in those embodiments where a coil is used to arterialize the vein of interest, a pusher bar as is known in the art.

The guidewire used to facilitate the delivery of the autoretroperfusion system 100 into a vessel by providing support to the components thereof. The guidewire may comprise any guidewire known in the art. Furthermore, the distal end of the guidewire may comprise a plurality of impedance electrodes that are capable of taking measurements of the size the vessel in which the guidewire is inserted through the use of impedance technology. Additionally, in at least one embodiment, the impedance electrodes may be further capable of communicating such measurements to the remote module 180 through telemetry or other wireless means in a manner similar to the at least one sensor 166 of the distal end 154 of the second catheter 150. In at least one embodiment, the distal end of the guidewire may comprise two tetrapolar sets of impedance electrodes disposed on its distal-most tip.

Based on the information gathered by the impedance electrodes, a clinician can obtain accurate measurements of a selective region of a vessel. In this manner, the expandable balloon 158 coupled with the distal end 154 of the second catheter 150 may be properly sized and the amount of fluid or gas needed to inflate the expandable balloon 158 can be determined prior to introducing the second catheter 150 into the vein of interest. For example, a clinician can use the plurality of impedance electrodes on the guidewire to obtain measurements of the size and shape of the sub-branches of the coronary sinus. Details regarding the specifications and use of the impedance electrodes are described in detail in the currently pending U.S. patent application Ser. No. 10/782,149 entitled "System and Method for Measuring Cross-Sectional Areas and Pressure Gradients in Luminal Organs," and filed on Feb. 19, 2004, which is hereby incorporated by reference herein in its entirety.

Figure 5:
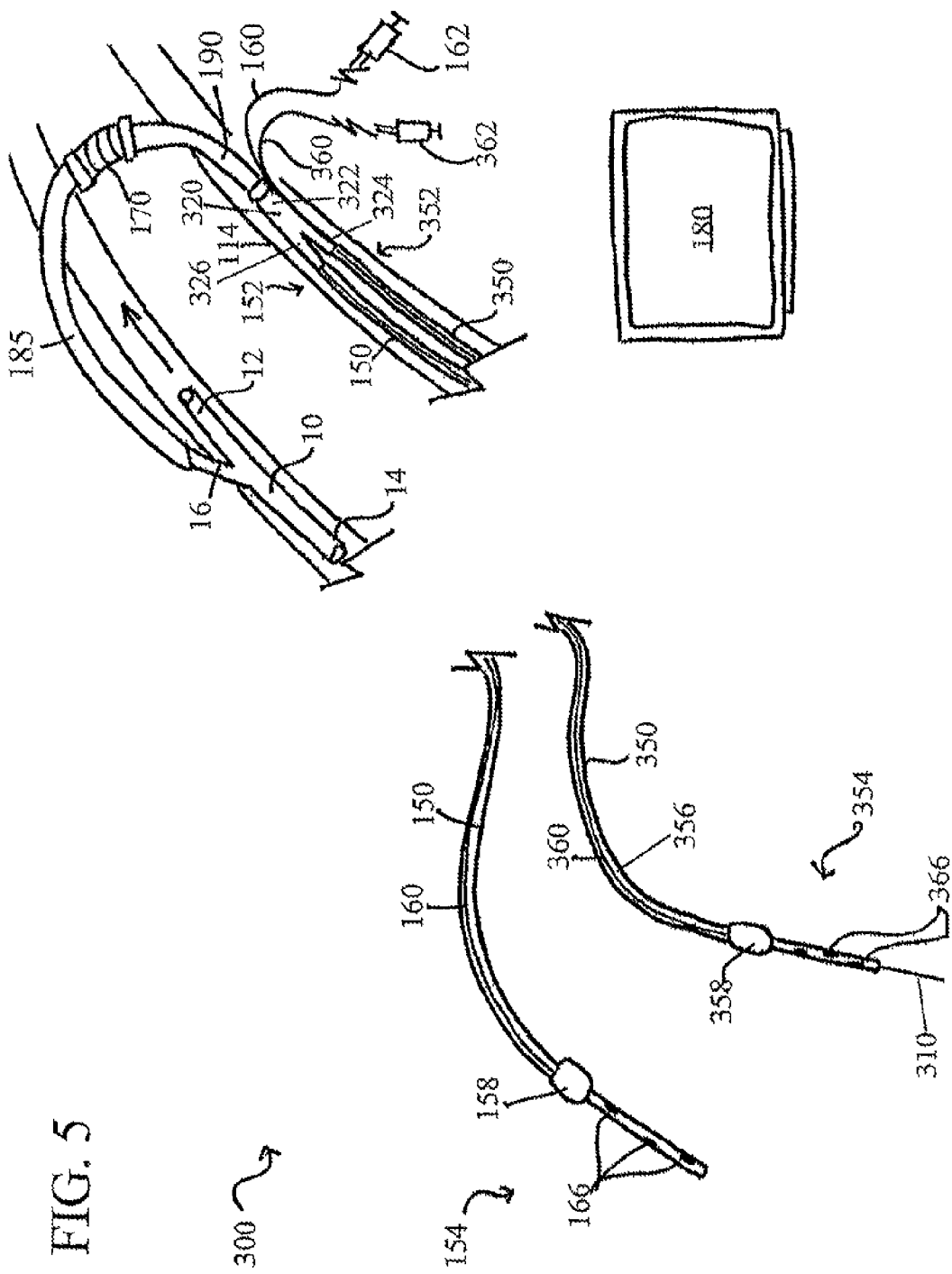
FIG. 5 shows the components of an autoretroperfusion system that can be used to deliver retroperfusion therapy to ischemic tissue, according to at least one embodiment of the present disclosure.

Now referring to FIG. 5, components of a simultaneous selective autoretroperfusion system 300 are shown. The simultaneous selective autoretroperfusion system 300 (the "SSA system 300") are configured identically to the autoretroperfusion system 100 except that the SSA system 300 further comprises a third catheter 350 and a Y connector 320, both configured for placement within the venous vessel wall 114. Specifically, the SSA system 300 comprises the catheter 10, the second catheter 150, the third catheter 350, the connector 170, and the Y connector 320. It will be understood that the SSA system 300 can also further comprise the first graft 185 and/or the second graft 190, and the remote module 180 as described in connection with autoretroperfusion system 100.

The third catheter 350 is configured for placement within the venous vessel wall 114 adjacent to the second catheter 150. The third catheter 350 is configured identically to the second catheter 150 and comprises a flexible tube having a proximal end 352, a distal end 354 and at least one lumen 356 extending between the proximal end 352 and the distal end 354. Both the proximal end 352 and the distal end 354 of the third catheter 350 are open and in communication with the at least one lumen 356 of the third catheter 350, thereby allowing blood to flow into the at least one lumen 356 through the proximal end 352 and out of the distal end 354 back into the venous vessel 114.

The third catheter 350 may be any catheter known in the art that is capable of intravascular insertion and advancement through the venous system. The third catheter 350 may comprise any appropriate material, including without limitation, polyurethane or silicone rubber. In at least one embodiment, the third catheter 350 is configured to receive a guidewire 310 (see FIGS. 5 and 6) through the at least one lumen 356 in order to facilitate the intravascular delivery of the distal end 354 of the third catheter 350 into the desired location of the venous vessel 114. Furthermore, the third catheter 350 is coated with heparin or any other suitable anti-coagulant prior to insertion in order to facilitate the extended placement of the third catheter 350 within the venous vessel 114.

As shown in FIG. 5, the distal end 354 of the third catheter 350 further comprises an expandable balloon 358 coupled with the external surface of the third catheter 350. In operation, the expandable balloon 358 can be used to anchor the distal end 354 of the third catheter 350 in the desired location within the venous vessel wall 114. The expandable balloon 358 may be any expandable balloon that is appropriate for insertion within a vessel and can be formed of any material suitable for this function, including without limitation, polyethylene, latex, polyestherurethane, polyurethane, sylastic, silicone rubber, or combinations thereof.

Similar to the expandable balloon 158 of the second catheter 150, the expandable balloon 358 is capable of being controlled by a clinician such that it can inflate and/or deflate to the proper size. The appropriate size of the expandable balloon 358 can be determined through any technique known in the art, including without limitation, by measuring the compliance of the expandable balloon 358 ex vivo or in vivo. Furthermore, when the guidewire 310 is used to facilitate the delivery of the distal end 354 of the third catheter 350 into the desired location within the venous vessel wall 114, the electrodes on the distal end of the guidewire 310 may be used to accurately measure the cross-sectional area of the venous vessel 114 such that the expandable balloon 358 can be precisely sized prior to insertion into the vein 114.

In this at least one embodiment, the expandable balloon 358 is in fluid communication with a secondary lumen 360 disposed within the at least one lumen 356 of the third catheter 350. In this example, the secondary lumen 360 is coupled with a balloon port 362 that extends from the proximal end 352 of the third catheter 350. Accordingly, when the SSA system 300 is positioned within a patient, the balloon port 362 can be easily accessed by a clinician, subcutaneously, percutaneously or otherwise, and used to inflate or deflate the expandable balloon 358 with no or minimal invasion to the patient.

Similar to the second catheter 150, the distal end 354 of the third catheter 350 may further comprise at least one sensor 366 coupled therewith. The at least one sensor 366 may be configured identically to the at least one sensor 166 of the second catheter 150 and, accordingly, the at least one sensor 366 may be used to monitor the pressure of blood flow through the at least one lumen 356 of the third catheter 350 or the venous vessel 114 or to monitor the pH or the concentrations of carbon dioxide, lactate, or cardiac enzymes within the blood. Furthermore, the at least one sensor 366 is capable of communicating the data it gathers to the remote module 180 through the use of a wireless technology such that a clinician can easily access the gathered information on a real-time basis or otherwise. In at least one embodiment, the at least one sensor 366 is disposed on the distal end 354 of the third catheter 350 distally of the expandable balloon 358; however, it will be understood that the at least one sensor 366 may be disposed in any location on the distal end 354 of the third catheter 350.

The Y connector 320 of the SSA system 300 comprises flexible material and has a proximal end 322, a distal end 324 and at least one lumen 326 extending between the proximal and distal ends 322, 324. The proximal end 322 of the Y connector 322 is open and configured to be securely coupled with the graft 190. The distal end 324 of the Y connector 322 comprises two open ends which extend from the body of the Y connector 322 in a substantially Y-shaped configuration. The two open ends of the distal end 324 of the Y connector 322 thereby divide the at least one lumen 326 into two separate channels and thus the blood flowing through the at least one lumen 326 is yet again bifurcated.

The proximal end 152 of the second catheter 150 is coupled with one of the two open ends of the distal end 324 of the Y connector 322, thereby receiving a portion of the blood flow that flows through the at least one lumen 326 of the Y-connector. Similarly, the proximal end 352 of the third catheter 350 is coupled with the other open end of the distal end 324 of the Y connector 322 and, thus, the third catheter receives a portion of the blood flow that flows through the at least one lumen 326 of the Y-connector. In this manner, the SSA system 300 can be used to simultaneously retroperfuse more than one ischemic area of the body.

Figure 6:
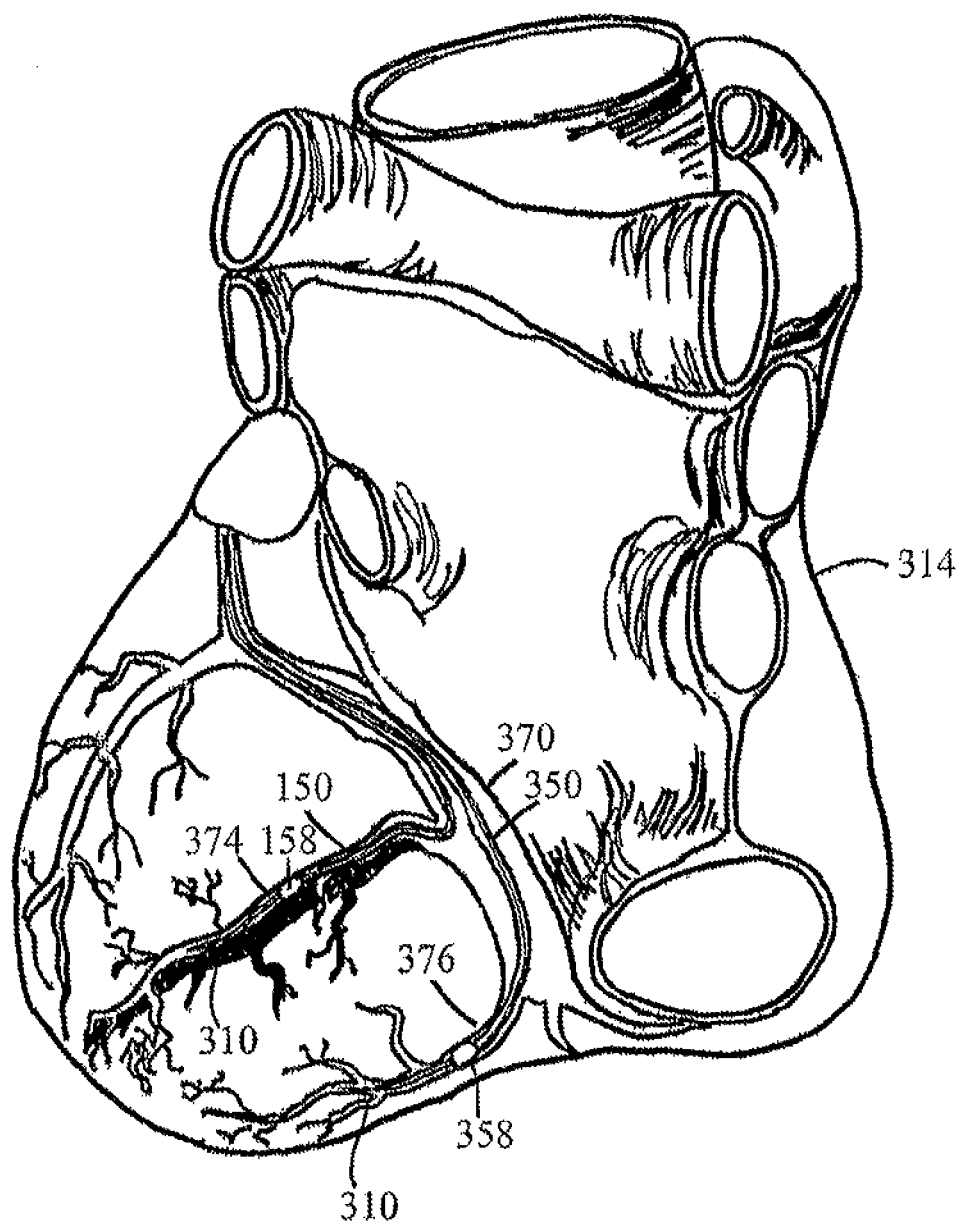
FIG. 6 shows a view of the base and diaphragmatic surface of a heart with the distal ends of two components of the autoretroperfusion system of FIG. 5 positioned therein such that the autoretroperfusion system can deliver simultaneous selective autoretroperfusion therapy thereto, according to at least one embodiment of the present disclosure.

In application, the second catheter 150 and the third catheter 350 are positioned adjacent to each other within the venous vessel wall 114 as shown in FIG. 5. Furthermore, the distal ends 154, 354 of the second and third catheters 150, 350, respectively, may be placed within different veins such that the arterial blood is delivered to selective portions of ischemic tissue. For example, as shown in FIG. 6, in at least one embodiment the SSA system 300 can be applied to a heart 314 to provide an arterial blood supply to two separate coronary veins, or sub-branches, simultaneously. In this at least one embodiment, the distal ends 154, 354 of the second and third catheters 150, 350 are both advanced through the coronary sinus 370. As the diameter of the coronary sinus 370 ranges from about 10 to about 20 millimeters, cannulating the coronary sinus 370 with both the second and third catheters 150, 350 does not occlude the normal antegrade flow of the blood therethrough. Upon reaching the veins or sub-branches of interest, the distal ends 154, 354 of the second and third catheters 150, 350 are each independently positioned within the veins of interest. In the example shown in FIG. 6, the second catheter 150 is positioned within the interventricular vein 374 and the distal end 354 of the third catheter 350 is positioned within the middle cardiac vein 376. As with autoretroperfusion system 100, the expandable balloons 158, 358 are inflated through balloon ports 162, 362, respectively (shown in FIG. 5), such that the distal ends 154, 354 of the second and third catheters 150, 350 are securely anchored in the desired location within the veins of interest. In this manner, the SSA system 300 can deliver controlled arterial blood flow to, and thus arterialize, two areas of the heart 314 simultaneously.

In at least one embodiment of the SSA system 300, the components of the system 300 are available in a package. Here, the package may also contain sterile syringes with the fluids to be injected into the balloon ports 162, 362 to inflate the expandable balloons 158, 358, respectively. Furthermore, the package may also contain devices to facilitate delivery of the SSA system 300 such as arterial and venous access devices, a delivery catheter, at least two guidewires (configured as described in connection with the delivery of autoretroperfusion system 100), an introducer to maintain the catheter 10 in the collapsed position during delivery and, in those embodiments where a coil is used to arterialize the vein of interest, a pusher bar as is known in the art.

Figure 7:
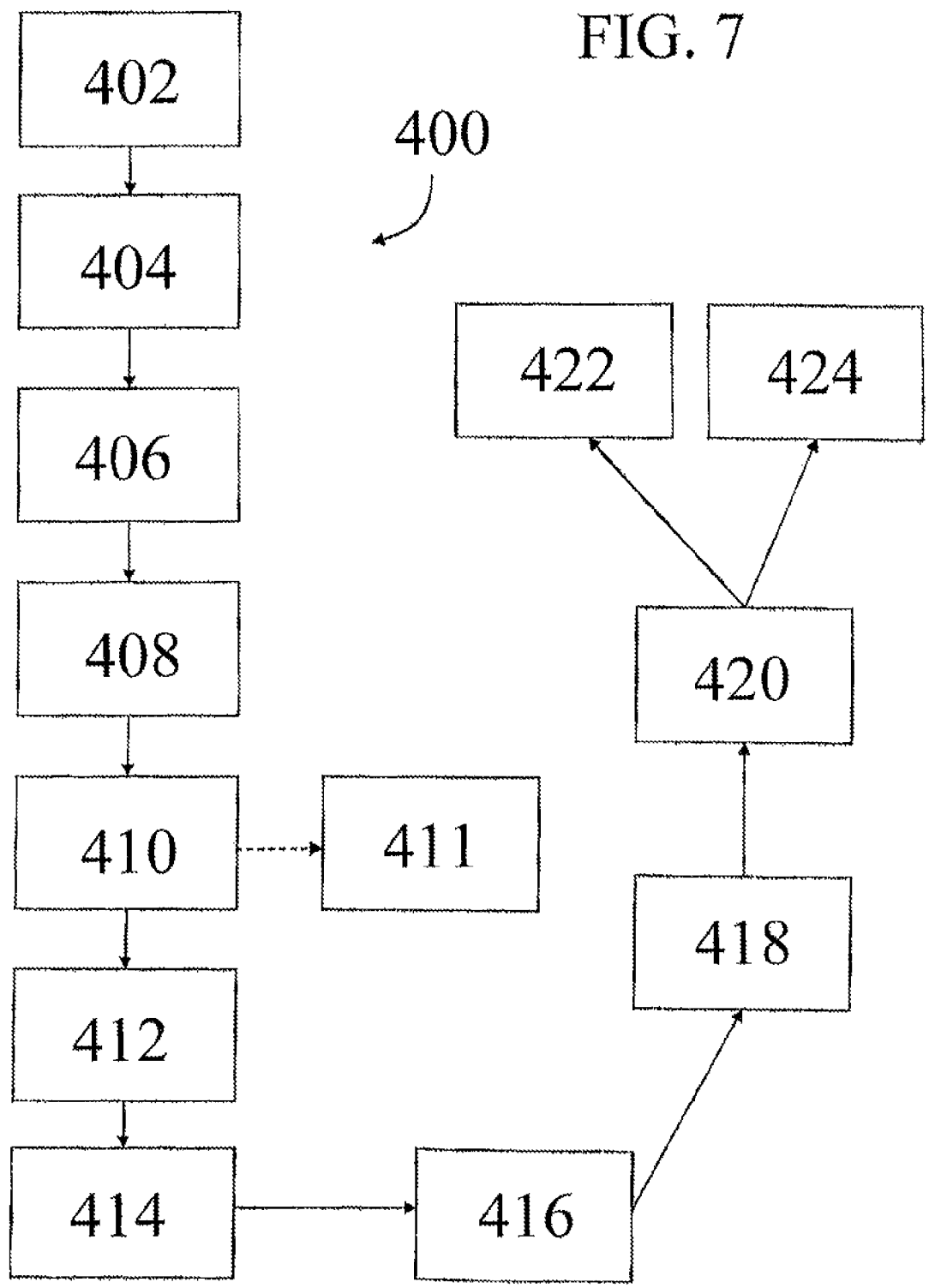
FIG. 7 shows a flow chart of a method for delivering autoretroperfusion therapy, according to at least one embodiment of the present disclosure.

Now referring to FIG. 7, a flow chart of a method 400 for performing automatic retroperfusion using the system 100 is shown. While the method 400 is described herein in connection with treating a heart through catheterization of the coronary sinus, it will be understood that the method 400 may be used to perform autoretroperfusion on any organ or tissue in need of retroperfusion treatment and/or other areas near the coronary sinus, such as the great cardiac vein, for example.

Method 400, and the embodiments thereof, can be performed under local anesthesia and do not require any arterial sutures. Further, once implanted, the system 100 can deliver chronic treatment to the patient as the system 100 is capable of remaining within a patient's vascular system for an extended period of time. In this manner, the system 100 and method 400 can be used to treat no-option patients and greatly enhance their quality of life.

As shown in FIG. 7, in one approach to the method 400, at step 402 an artery 502 of interest is percutaneously punctured under local anesthesia with a conventional artery access device or as otherwise known in the art. For example and without limitation, in at least one embodiment, an 18 gauge needle is inserted into the femoral or subclavian artery. At step 404, the catheter 10 housed in a collapsed position within an introducer 504 (see FIG. 8A) is inserted into the artery 502 of interest. After the distal end 14 of the catheter 10 is positioned in the desired location within the artery 502, the introducer 504 is proximally withdrawn from the artery 502 as shown in FIG. 8B, leaving the catheter 10 positioned therein.

Figure 8C:
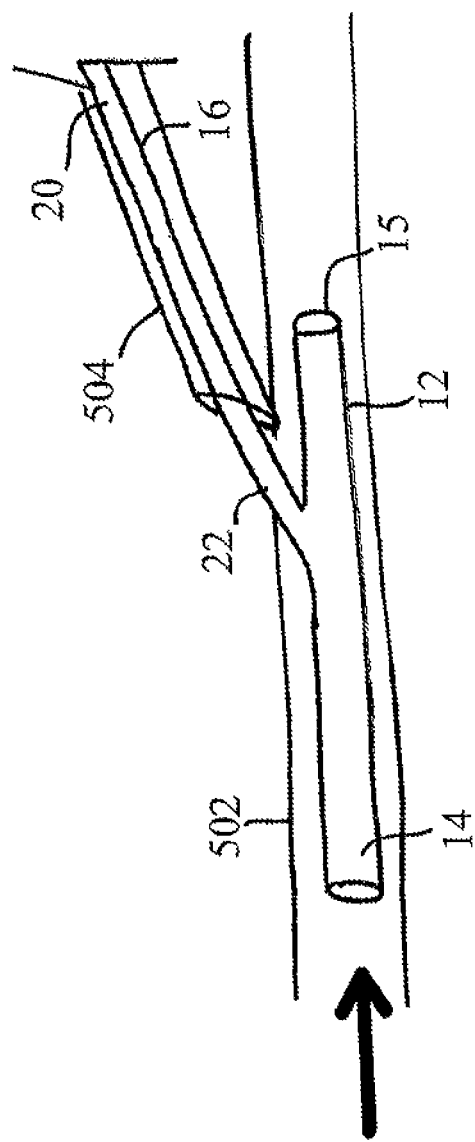
FIGS. 8C and 8D show side views of the introducer of FIG. 8A being removed from an arterial vessel, thereby deploying the projection cannula of the catheter of FIG. 1, according to at least one embodiment of the present disclosure.
Figure 8D:
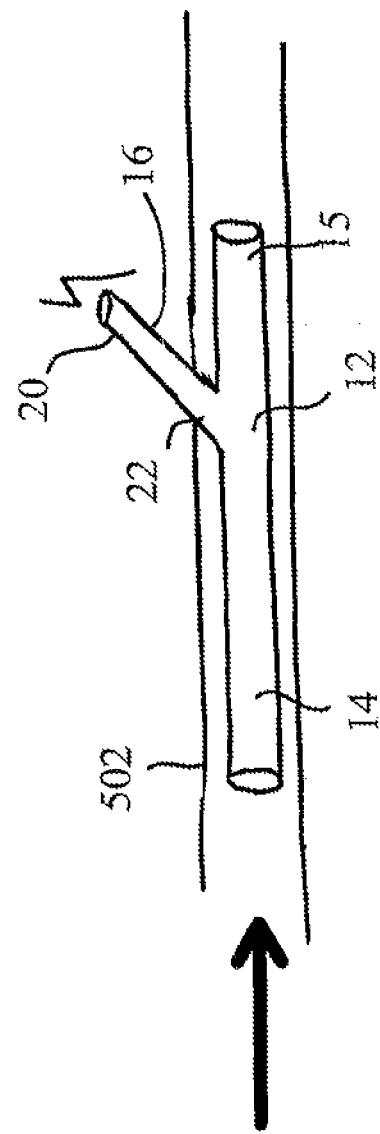

In at least one embodiment, the projection cannula 16 is configured such that when the introducer 504 is withdrawn in a proximal direction, the proximal end 12 of the catheter 10 is released from the introducer 504 before the proximal end 20 of the projection cannula 16 is released from the introducer 504. In this manner, the proximal end 12 of the catheter 10 is delivered within the interior of the arterial wall 502, while the projection cannula 16 remains housed within the interior of the introducer 504 as shown in FIG. 8C. Furthermore, because the introducer 504 no longer applies downward pressure to the projection cannula 16 relative to the proximal end 12 of the catheter 10, the projection cannula 16 is allowed to shift from the collapsed position to the expanded position and therefore extends in a direction that is not parallel with the artery 502 or the body of the catheter 10. In this manner, as shown in FIGS. 8C and 8D, the proximal end 20 of the projection cannula 16 is directed through the opening formed in the arterial wall 502 by the introducer 504.

Accordingly, when the catheter 10 is positioned within the artery 502, the antegrade blood arterial blood flow is allowed to continue through the artery 502 through the proximal end 12 of the catheter 10, while only a portion of the arterial blood is rerouted through the projection cannula 16 and into the veins 506 of interest. In this manner, the normal blood flow through the artery 502 is not inhibited by operation of the autoretroperfusion system 100. Furthermore, in addition to bifurcating the blood flowing through the artery 502, the projection cannula 16 traversing the arterial wall 502 further functions to anchor the catheter 10 in the desired position within the artery 502.

Figure 8E:
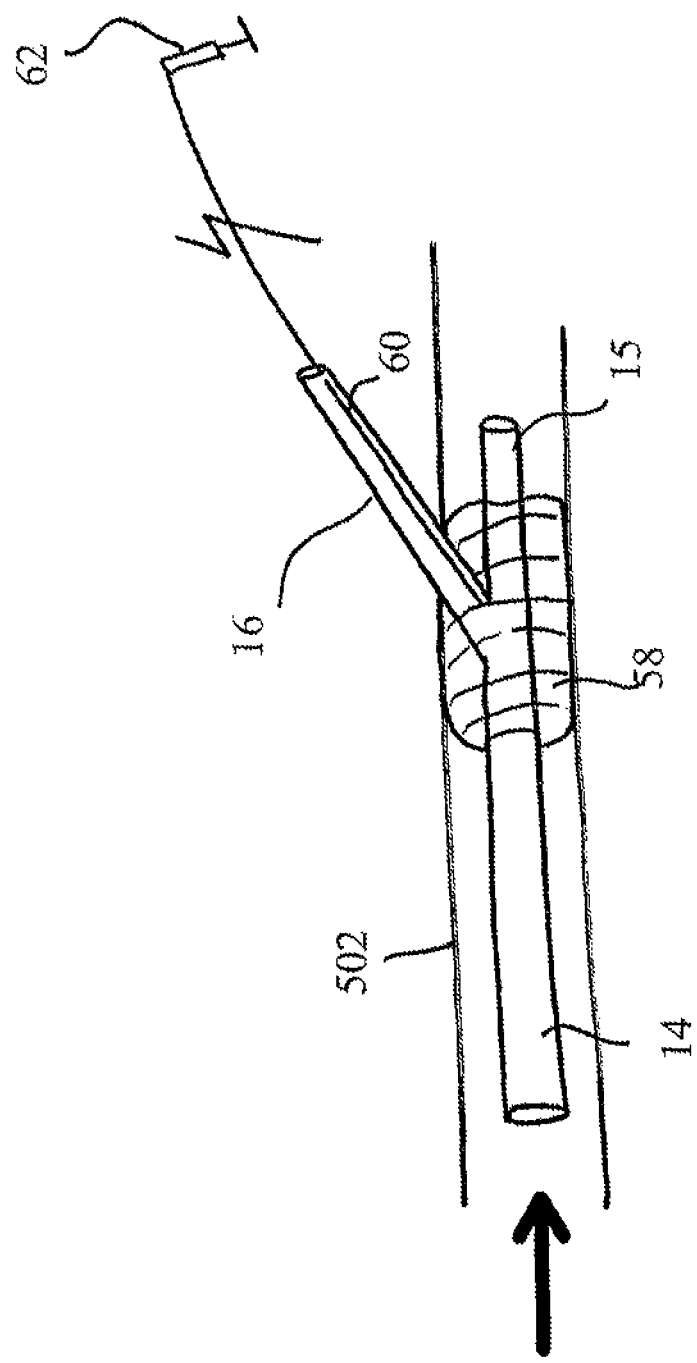
FIG. 8E shows a side view of the catheter of FIG. 1 anchored within an arterial vessel through the use of an expandable balloon, according to at least one embodiment of the present disclosure.

In the embodiment where the catheter 10 further comprises the expandable balloon 58 (see FIG. 1), step 404 may further comprise inflating the expandable balloon 58 to the desired size by injecting fluid into the balloon port 62. In this manner, the expandable balloon 58 functions to further anchor the catheter 10 in the desired location within the artery 502 and seal the opening in the artery 502 through which the projection cannula 16 projects (see FIG. 8E).

At step 406, a vein 506 of interest is percutaneously punctured under local anesthesia with a conventional venous access device or as otherwise known in the art. For example and without limitation, in at least one embodiment, an 18 gauge needle is inserted into the femoral or subclavian vein. At step 408, a delivery catheter 508 is inserted into and advanced through the vein 506 to catheterize the coronary sinus ostium. A guidewire 510 is then inserted at step 410 into the delivery catheter 510 and advanced into the lumen of the vein 506 through the distal end of the delivery catheter 510. Furthermore, the guidewire 510 is advanced into the region of interest by use of x-ray (i.e. fluoroscopy), direct vision, transesophageal echocardiogram, or other suitable means or visualization techniques.

Figure 9:
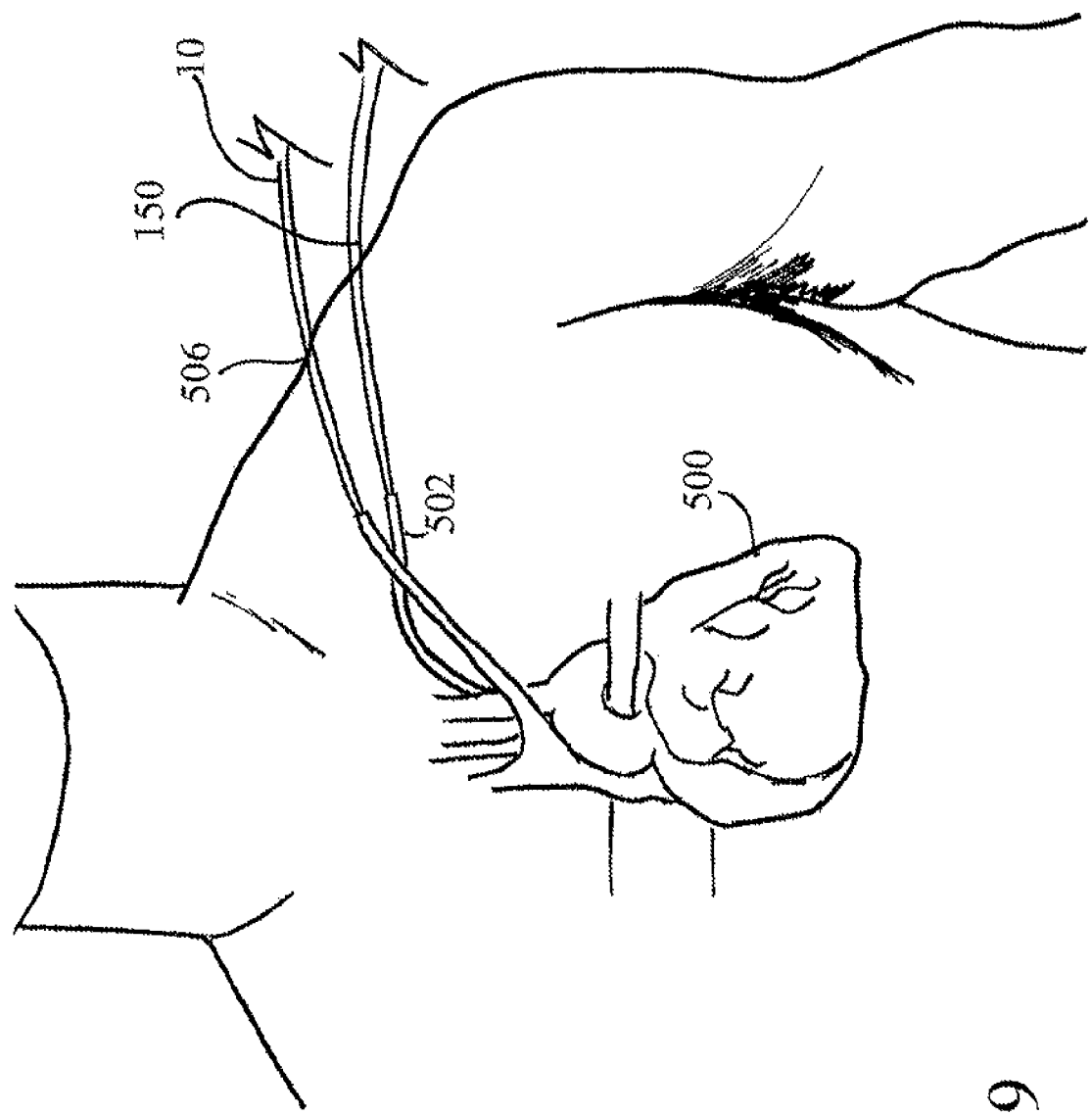
FIG. 9 shows a schematic view of the autoretroperfusion system of FIG. 5 as applied to a heart, according to at least one embodiment of the present disclosure.
Figure 10:
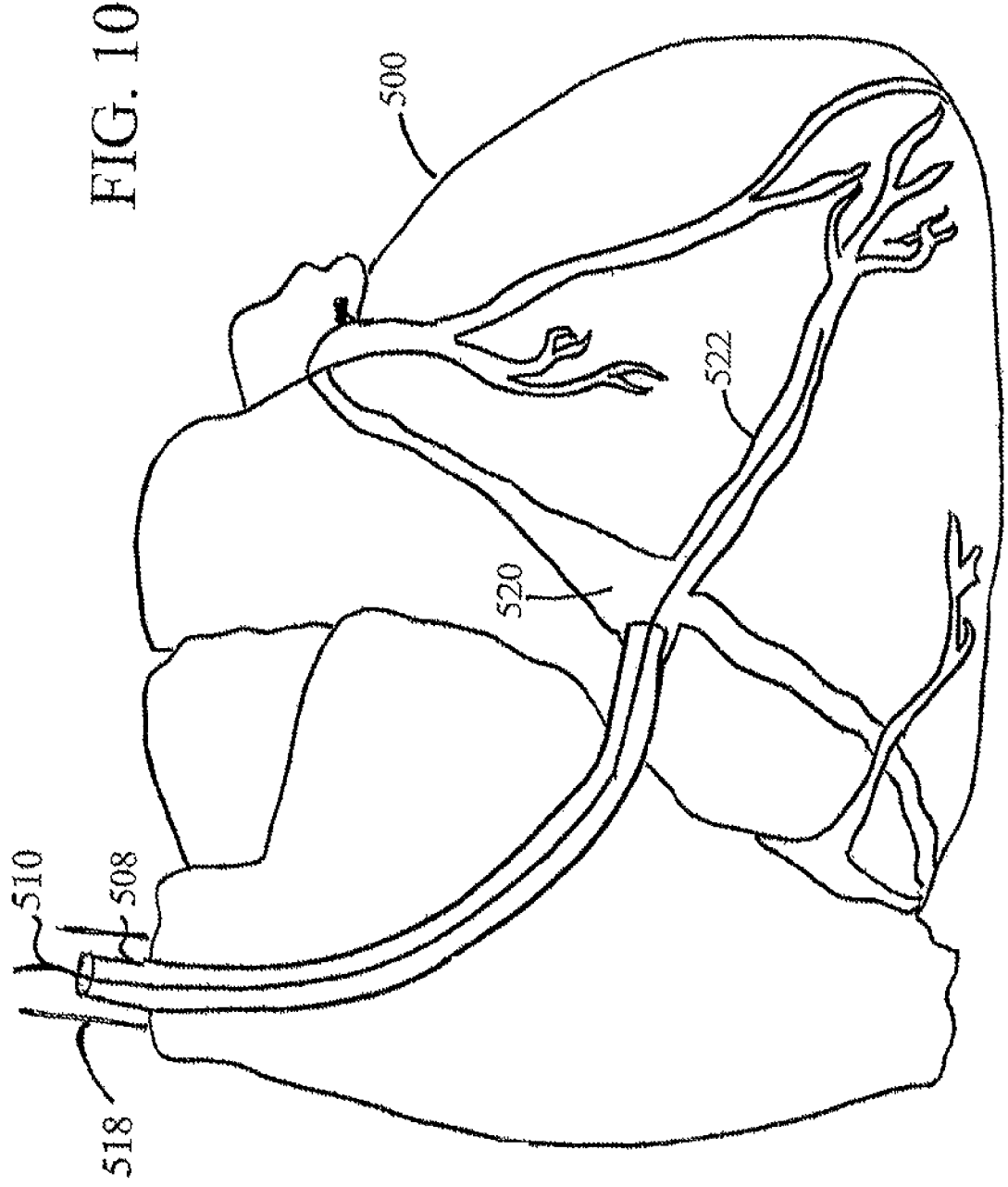
FIG. 10 shows a schematic view of the autoretroperfusion system of FIG. 5 as applied to a heart, according to at least one embodiment of the present disclosure.

FIGS. 9 and 10 show schematic views of the method 400 as applied to a heart 500. Specifically, in this at least one embodiment, at steps 402 and 404 the artery 502, which in FIG. 9 comprises the subclavian artery, is punctured and the catheter 10 is inserted and positioned therein. Further, at step 406 the vein 506, which in FIG. 9 comprises the subclavian vein, is punctured and at step 408 the delivery catheter 508 is advanced through the superior vena cava 518 and into the coronary ostium of the coronary sinus 520. As shown in FIG. 10, at step 410, the guidewire 510 is advanced through the coronary sinus 520 and into the vein of interest, which, in this at least one embodiment, comprises the posterior vein 522 of the heart 500.

Now referring back to FIG. 7, the guidewire 510 inserted into the vein 506 at step 410 may further comprise a plurality of impedance electrodes as previously described herein. In this approach, the guidewire 510 may be used at optional step 411 to determine the size of the vessel of interest through use of the plurality of impedance electrodes disposed thereon. In this manner, a clinician can use the measurements generated by the impedance electrodes to select a properly sized expandable balloon 158 for use in connection with the second catheter 150. By using a precisely sized expandable balloon 158 and inflation volume, the clinician can ensure that the distal end 154 of the second catheter 150 is securely anchored within the vessel of interest without imposing an undue force on the venous vessel walls.

Figure 11:
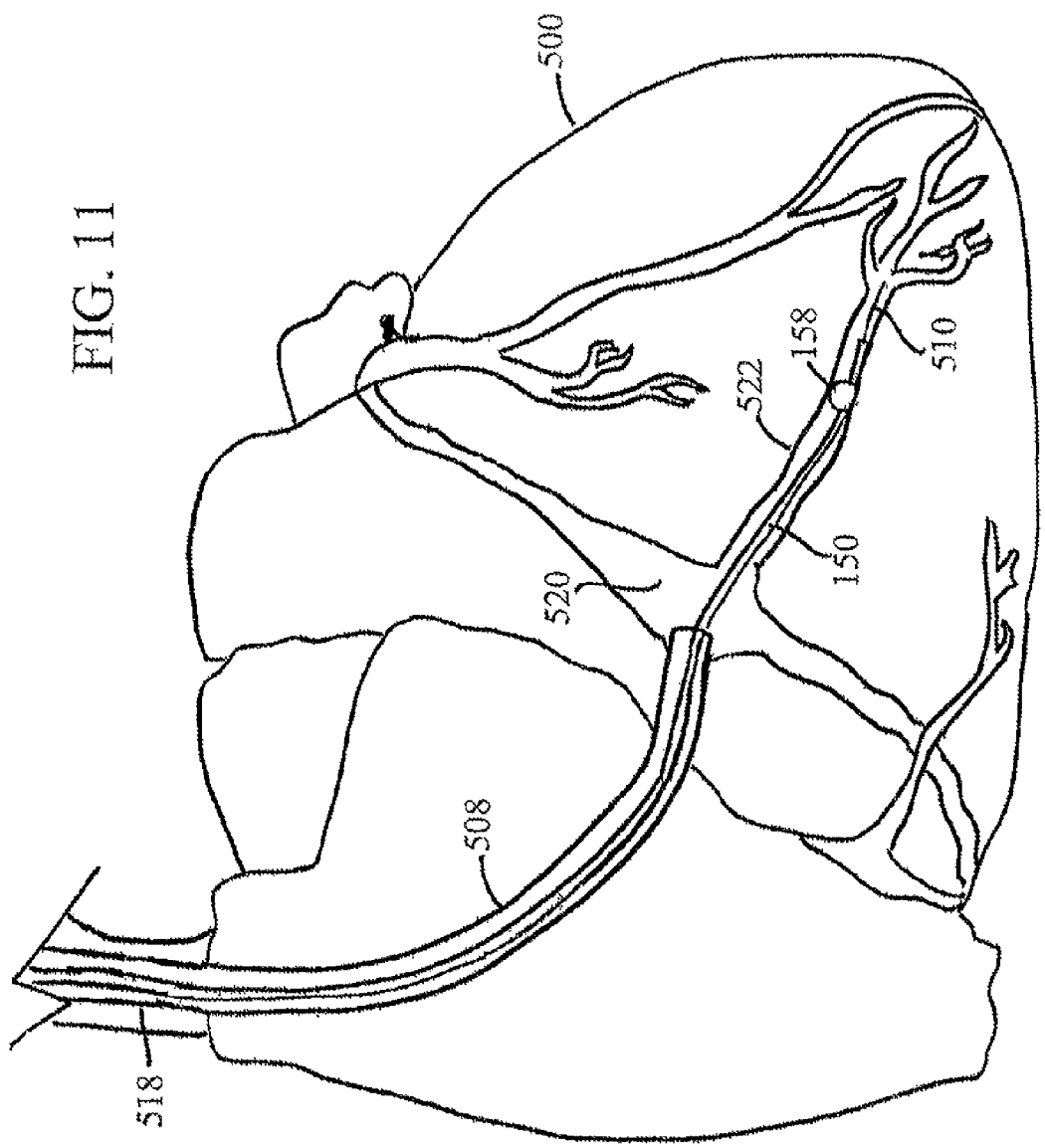
FIG. 11 shows a schematic view of a step of the method of FIG. 7 as the method is applied to a heart, according to at least one embodiment of the present disclosure.

After the guidewire 510 has been advanced into the vessel of interest at step 410 and, optionally, the dimensions of the vessel of interest have been measured at step 411, the method 400 advances to step 412. At step 412, the distal end 154 of the second catheter 150 is inserted into the delivery catheter 508 over the guidewire 510. Accordingly, the guidewire 510 is slidably received by the at least one lumen 156 of the second catheter 150. The distal end 154 of the second catheter 150 is then advanced over the guidewire 510 to the region of interest and the expandable balloon 158 of the second catheter 150 is inflated to anchor the distal end 154 within the targeted vessel. FIG. 11 shows a schematic view of the method 400, as applied to the heart 500, after step 412 has been completed. It will be understood that at any point after the distal end 154 of the second catheter 150 is positioned and anchored within the desired location in the targeted vessel, the delivery catheter 508 and the guidewire 510 may be withdrawn from the vein of interest.

After the distal end 154 of the second catheter 150 is secured within the targeted vessel, at step 414 the anastomosis between the vein 506 and the artery 502 is formed. Specifically, in at least one approach, the proximal end 20 of the projection cannula 16 of the catheter 10 is coupled with the proximal end 152 of the second catheter 150 by way of the connector 170. In the at least one embodiment of the system 100 comprising the first graft 185 and the second graft 190, the connector 170 may be coupled with the catheter 10 and the second catheter 150 via the first graft 185 and the second graft 190 to form an elongated anastomosis. Alternatively, in yet another approach, the connector 185 may be coupled with the catheter 10, via the proximal end 20 of the projection cannula 16 and the second catheter 150 via only the second graft 190. It will be understood that any combination of the catheter 10, the second catheter 150 and the first and second grafts 185, 190 may be used in connection with the connector 170 to form the desired anastomosis between the vein 506 and the artery 502.

After the anastomosis is formed and the arterial blood is allowed to flow through the anastomosis and thereby through the connector 170, at step 416 the connector 170 measures the flow rate, pressure and any other desired data of the arterial blood flow. The connector 170 transmits the collected data to the remote module 180 either through intravascularly placed leads or wirelessly, through telemetry or other means. In this manner, a clinician may easily view the blood flow data on the remote module 180 and assess the degree of pressure drop that will be required to preserve and gradually arterialize the vein 506.

At step 418, the pressure of the arterial blood flow through the system 100 is modified to transmit the desired pressure to the venous system. In this step 418 the pressure modification can be achieved through a clinician modifying the means of regulating the blood flow of the connector 170 through remote means or, in at least one embodiment of the system 100, inflating the internal expandable balloon of the second catheter 150 using the internal balloon port in order to partially occlude the flow of arterial blood through the at least one lumen 156 of the second catheter 150. Furthermore, in at least one alternative embodiment of the system 100, a clinician may deliver a resorbable stenosis configured to achieve the necessary pressure drop into the at least one lumen 156 of the second catheter 150 through means known in the art.

Alternatively, as previously described in connection with autoretroperfusion system 100, the remote module 180 may further comprise a computer or other processing means capable of being programmed to automatically analyze the data received from the connector 170 and, based on such data, determine the proper degree of adjustment required in the blood pressure flowing through the anastomosis. In this embodiment, at step 418, the remote module 180 automatically adjusts the means of regulating the blood flow of the connector 170 to achieve the optimal pressure drop. In this manner, the desired pressure drop between the arterial system and the venous system is immediately achieved and the risk of venous rupture is significantly reduced.

In step 420 the method 400 allows the arterial blood having a modified pressure to irrigate the vein 506 for a period of time such that the vein 506 properly arterializes. For example, and without limitation, the patient's venous system may be subjected to the reduced arterial pressure for about fourteen days to allow the vein 506 to adapt to the elevated blood pressure flowing therethrough.

After arterialization of the vein 506 is achieved, at step 422 the patient may optionally undergo a coronary venous bypass graft surgery and the components of the autoretroperfusion system 100 may be removed. However, as previously discussed, even with a properly arterialized vein 506, many patients that require retroperfusion therapy may still not be candidates for a coronary vein bypass graft surgery. In the event that the patient is unable to tolerate such a procedure, after the vein 506 has arterialized at step 420, the method 400 can progress directly to step 424. At step 424, the pressure modification of the arterial blood flowing through the second catheter 150 is ceased. Accordingly, pre-arterialized veins 506 are subjected to the full arterial pressure of the blood flowing through the anastomosis and second catheter 150. In at least one embodiment, a clinician can cease the pressure modification by adjusting the controller 170. Alternatively, in the at least one embodiment where the controller 170 can be automatically adjusted by the remote module 180, the remote module 180 can automatically adjust the controller 170 after the veins 506 have pre-arterialized. Further, where the pressure drop is achieved through the use of an internal expandable balloon positioned within the at least one lumen 156 of the second catheter, the clinician may deflate the internal expandable balloon through the internal balloon port and thereafter withdraw the deflated internal expandable balloon through the tertiary lumen of the second catheter and the internal balloon port. In yet another embodiment where a resorbable stenosis is used to achieve the pressure drop in the arterial blood as it flows through the second catheter 150, the resorbable stenosis can be configured to dissolve after the desired period of time, thereby gradually decreasing the influence the resorbable stenosis has on the pressure of the blood flowing through the at least one lumen 156 of the second catheter over a period of time. Accordingly, the autoretroperfusion system 100 can remain chronically implanted within the patient to deliver oxygen-rich blood to a targeted area of tissue over an extended period of time.

Figure 12:
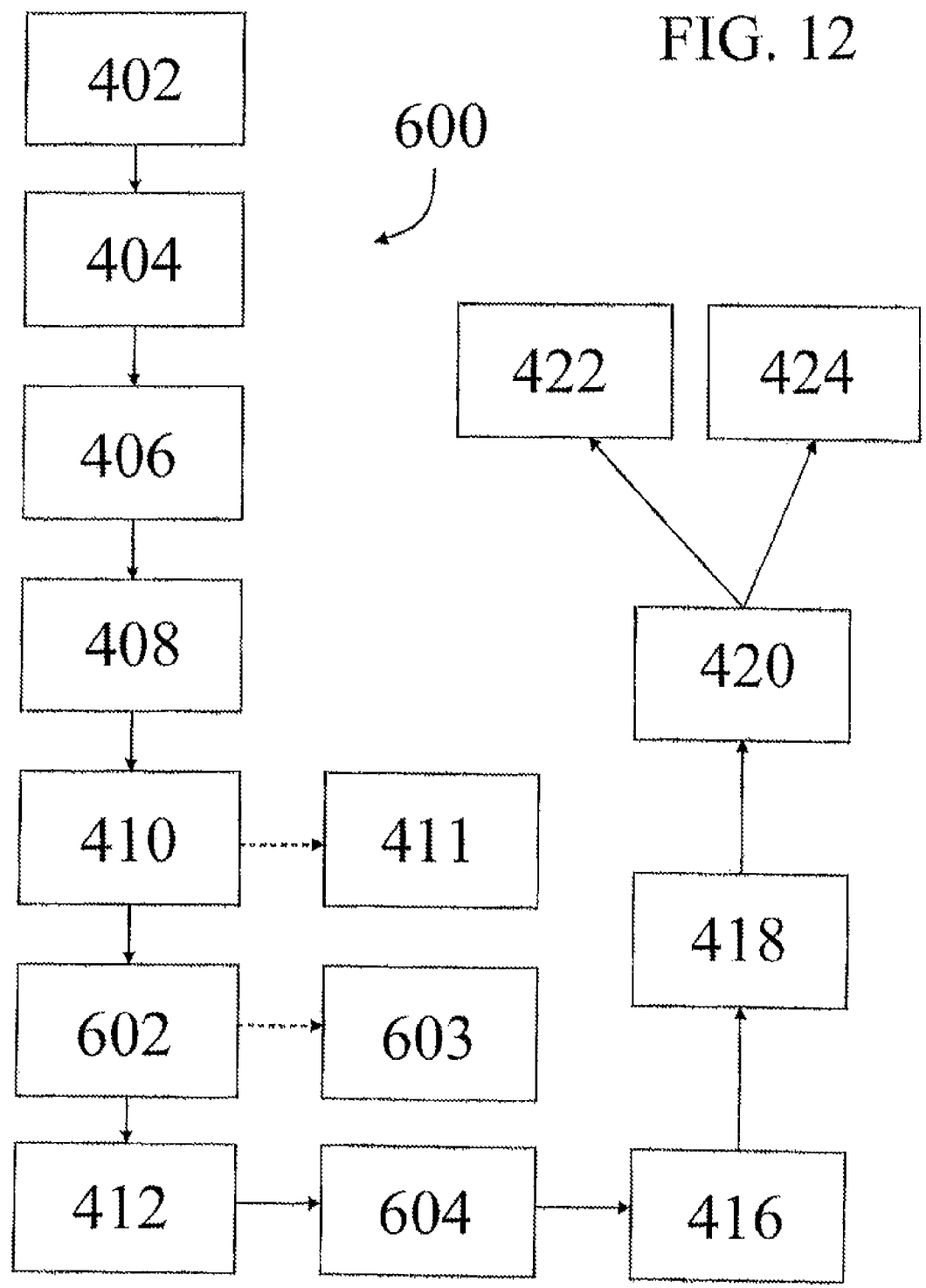
FIG. 12 shows a flow chart of a method for delivering simultaneously selective autoretroperfusion therapy, according to at least one embodiment of the present disclosure.

Now referring to FIG. 12, a flow chart of a method 600 for performing simultaneous selective retroperfusion using the SSA system 300 is shown. While the method 600 is described herein in connection with treating a heart 500 through catheterization of the coronary sinus 520, it will be understood that the method 600 may be used to perform autoretroperfusion on any organ or tissue in need of retroperfusion treatment. The reference numerals used to identify the steps of method 600 that are included in the description of method 400 designate like steps between the two methods 400, 600. As such, like steps between the two methods 400, 600 will not be discussed in detail with respect to the method 600 and it will be understood that such description can be obtained through the description of the method 400.

Method 600, and the embodiments thereof, can be performed under local anesthesia and does not require arterial sutures. Further, once implanted, the SSA system 300 can deliver simultaneous chronic treatment to multiple ischemic locations as the system 300 is capable of remaining within a patient's vascular system for an extended period of time and selectively retroperfusion more than one sub-branch of a vein 506.

The method 600 progresses through steps 402 through 410 as previously described in connection with the method 400. After the guidewire 510 is advanced through the coronary sinus 520 and into the first vein of interest, a second guidewire 610 is inserted at step 602 into the delivery catheter 508 adjacent to the guidewire 510, and advanced into the lumen of the vein 506 through the distal end of the delivery catheter 510. The second guidewire 610 is then advanced into a second region of interest by use of x-ray (i.e. fluoroscopy), direct vision, transesophageal echocardiogram, or other suitable means or visualization techniques. The second guidewire 610 is configured similar to the guidewire 510 and is capable of functioning the in the same manner.

Figure 13:
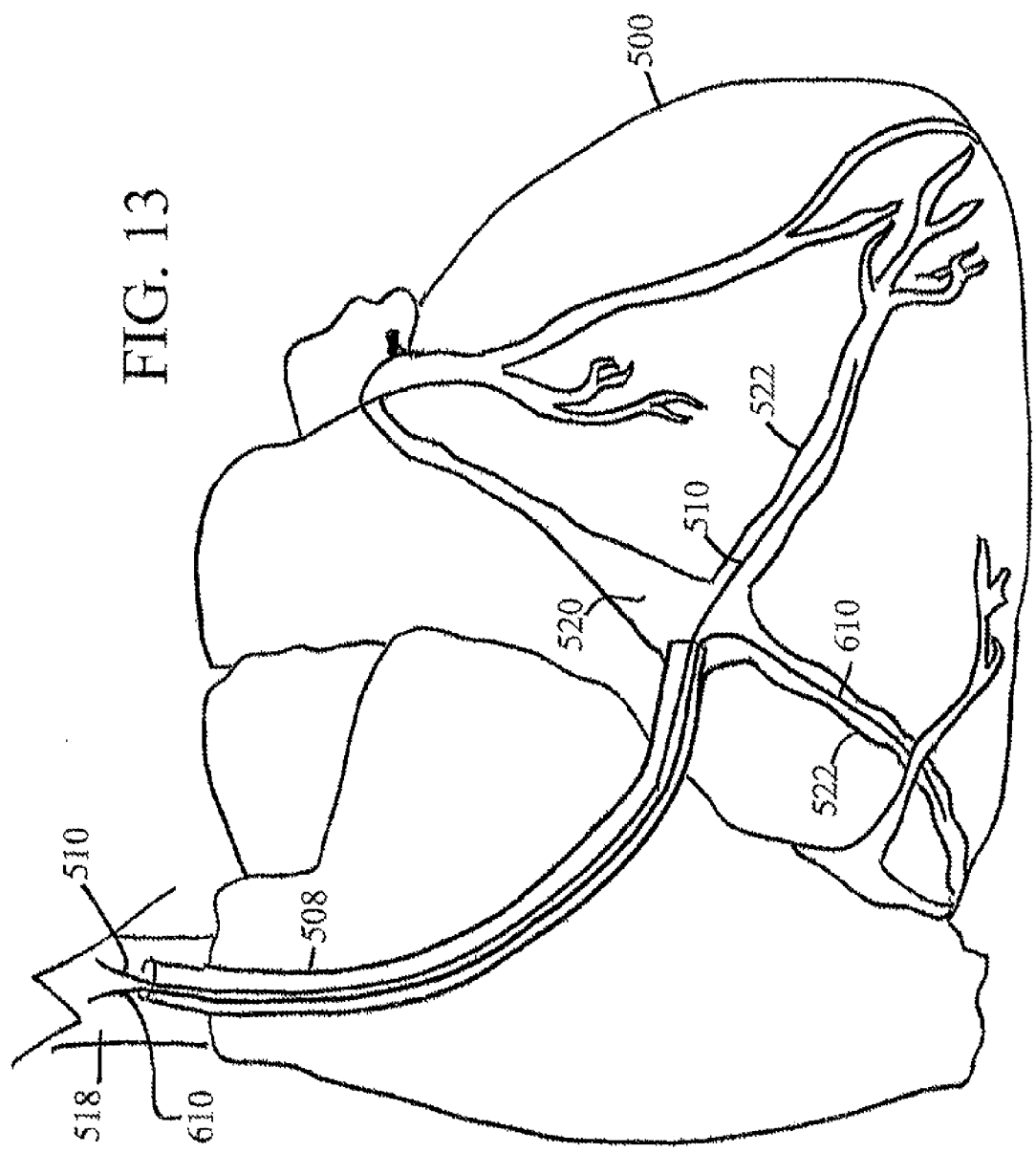
FIG. 13 shows a schematic view of a step of the method of FIG. 12 as the method is applied to a heart, according to at least one embodiment of the present disclosure.

FIG. 13 shows a schematic view of the method 600 as applied to a heart 500. Specifically, in this at least one embodiment, FIG. 13 shows the method 600 at step 602 wherein the guidewire 510 is inserted a first vein of interest, which comprises the posterior vein 522 of the heart 500, and the second guidewire 610 is inserted into a second vein of interest, which comprises the interventricular vein 622 of the heart 500.

Now referring back to FIG. 12, the guidewire 610 inserted into the second vein of interest in step 602 may further comprise a plurality of impedance electrodes as previously described with respect to the guidewire 510. In this embodiment, the guidewire 610 may be used at optional step 603 to determine the size of the second vessel of interest through use of the plurality of impedance electrodes disposed thereon. In this manner, a clinician can use the measurements generated by the impedance electrodes to select a properly sized expandable balloon 358 for use in connection with the third catheter 350. By using a precisely sized expandable balloon 358 and inflation volume, a clinician can ensure that the distal end 354 of the third catheter 350 is securely anchored within the second vessel of interest without imposing an undue force on the venous vessel walls.

Figure 14:
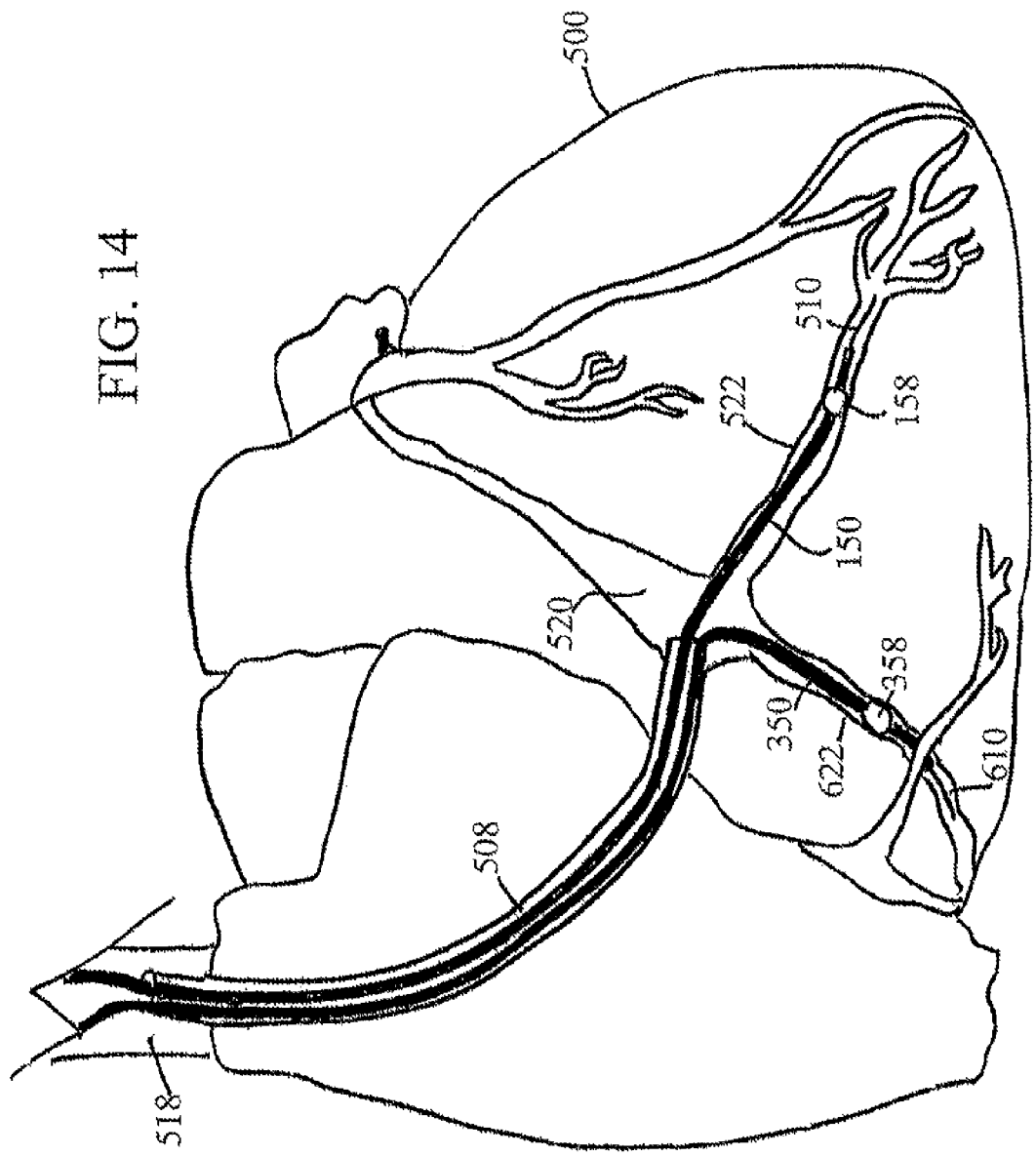
FIG. 14 shows a schematic view of a step of the method of FIG. 12 as the method is applied to a heart, according to at least one embodiment of the present disclosure.

After the guidewire 610 has been advanced into the second vessel of interest at step 602 and, optionally, the dimensions of the second vessel of interest have been measured at step 603, the method 600 advances to step 412 wherein the second catheter 150 is inserted over the guidewire 510 as described in connection with method 400. At step 604, the distal end 354 of the third catheter 350 is inserted into the delivery catheter 508 over the second guidewire 610. Accordingly, the second guidewire 610 is slidably received by the at least one lumen 356 of the third catheter 350. The distal end 354 of the third catheter 350 is then advanced over the second guidewire 610 to the second region of interest and the expandable balloon 358 of the third catheter 350 is inflated to anchor the distal end 354 within the targeted vessel. FIG. 14 shows a schematic view of the method 600 at step 604 as applied to the heart 500. It will be understood that at any point after the distal ends 154, 354 of the second and third catheters 150, 350 are positioned and anchored in the desired locations within the targeted vessels, the delivery catheter 508 and the guidewires 510, 610 may be withdrawn from the vein 506.

After both the distal end 154 of the second catheter 150 and the distal end 354 of the third catheter 350 are secured within the targeted vessels, the method 600 proceeds to step 414 where the anastomosis is formed between the vein 506 and the artery 502 as described in connection with method 400. Thereafter, the method 600 advances through steps 416 through 424 as described in connection with the method 400. Furthermore, at step 418, it will be recognized that a clinician can independently adjust the pressure drop through the second and third catheters 150, 350 in the event that an internal expandable balloon is used in either or both catheters 150, 350 or resorbable stenosis are employed within the at least one lumens 156, 356 of the second and third catheters 150, 350. Alternatively, in the at least one embodiment where the controller 170 comprises a means for regulating the blood flow through the anastomosis, the pressure of the arterial blood flowing through both the second and third catheters 150, 350 may be substantially the same.

As described herein, the method 600 may be used to simultaneously and immediately treat two different ischemic areas of a tissue through the use of one minimally to non-invasive procedure. Furthermore, the method 600 can provide no-option patients with a viable treatment option that is not associated with contraindications for congestive heart failure, diabetes, or drug treatment.

Figure 15:
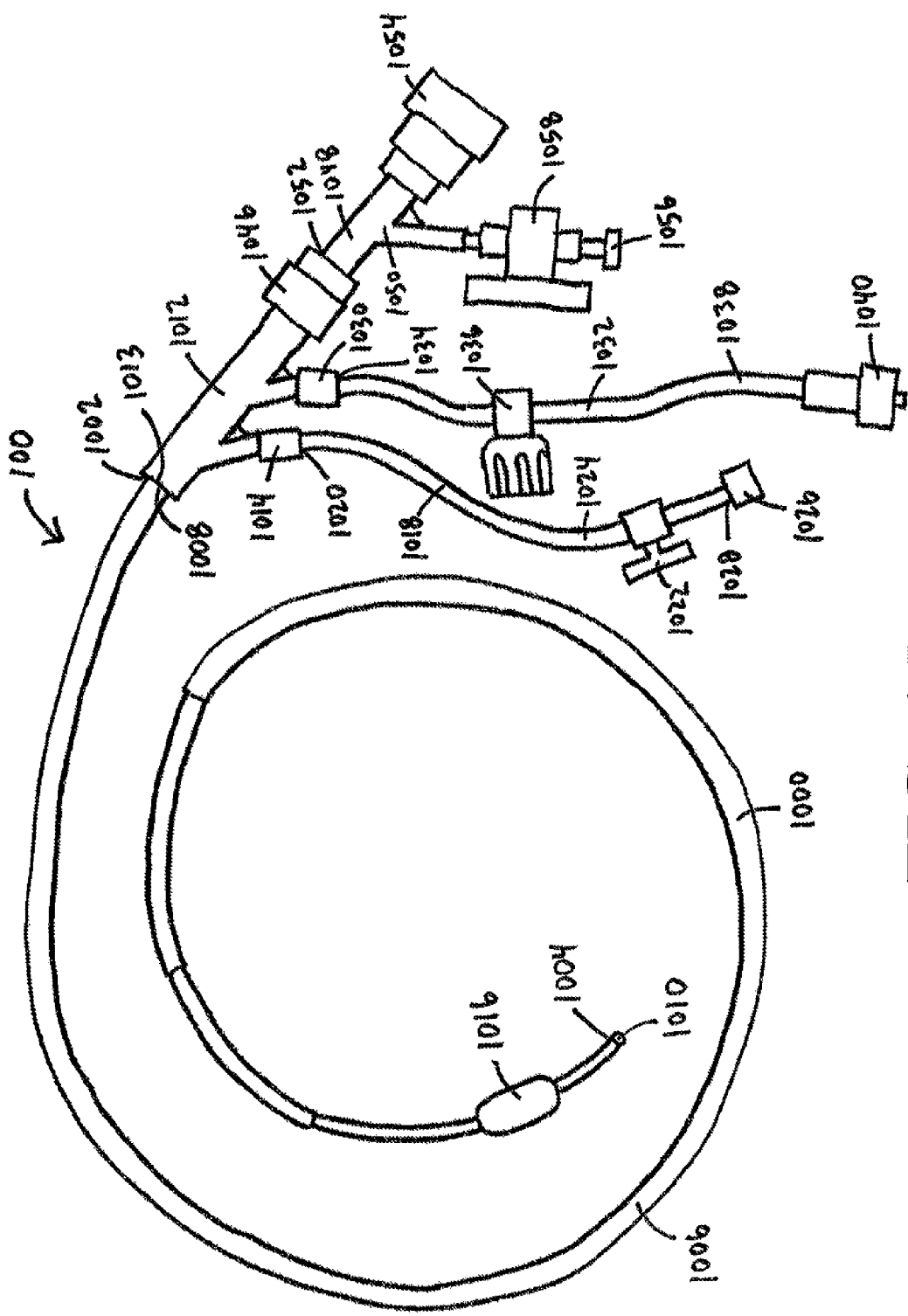
FIG. 15 shows an exemplary retroperfusion system, according to at least one embodiment of the present disclosure.

An additional embodiment of a perfusion system 100 of the present disclosure is shown in FIG. 15. As shown in FIG. 15, system 100 comprises a first catheter 1000 having a distal end 1004, a proximal end 1002, and defining a lumen 1006 therethrough, wherein at least a portion of first catheter 1000 is configured for insertion into a body of a patient, such as into a patient's heart or a patient's vein, for example. First catheter 1000, after insertion into a patient's vein or heart, for example, is capable of providing arterial blood (which is relatively rich in oxygen and other nutrients) thereto by way of transfer of arterial blood from, for example, a patient's artery, as described below, into a proximal catheter opening 1008, through lumen 1006, and out of distal catheter opening 1010. In such a fashion, for example, a system 100 can be referred to as an autoretroperfusion system 100, noting that no outside pumps are necessary (as the patient's own heart serves as the pump), and due to the retrograde nature of the perfusion with respect to such a use. Exemplary uses, as provided in detail herein, are to provide arterial blood, using system 100, to a patient's femoral vein, internal jugular vein, subclavian vein, and/or brachial cephalic vein. In an exemplary embodiment, first catheter 1000 may be tapered toward distal end 1004 to facilitate insertion into a patient.

Figure 16:
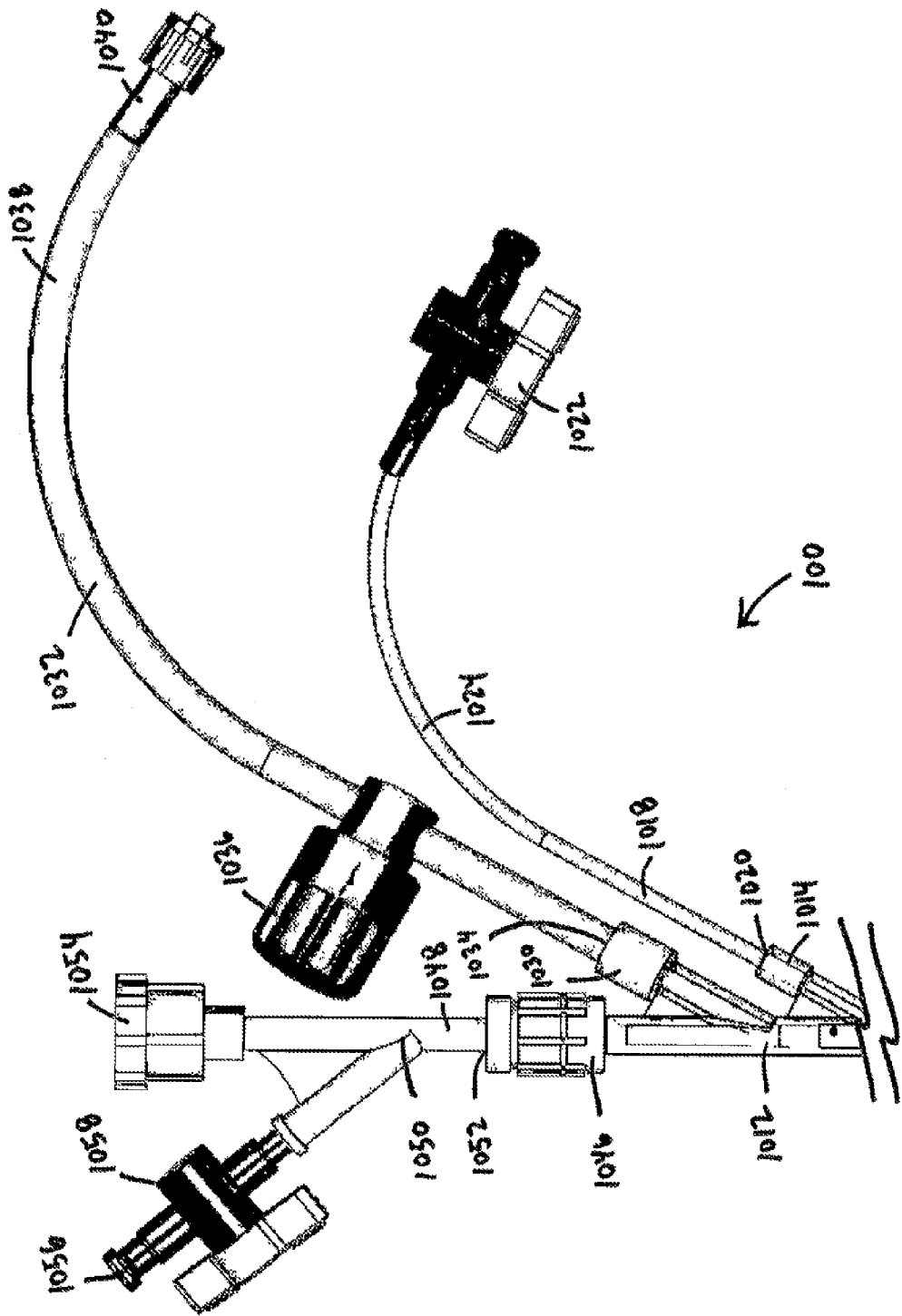
FIG. 16 shows a portion of an exemplary retroperfusion system, according to at least one embodiment of the present disclosure.

In at least one embodiment of system 100, and as shown in FIGS. 15 and 16, system 100 comprises a coupler 1012 having an outlet port 1013 and one or more additional ports to facilitate connection outside of the patient's body. For example, and as shown in FIGS. 15 and 16, coupler 1012 comprises an inflation port 1014, whereby fluid and/or gas introduced into inflation port 1014 can be used to inflate an expandable balloon 1016 positioned along first catheter 1000 at or near the distal end 1004 of first catheter 1000. As shown in the figures, and in at least one embodiment, an inflation tube 1018 may be coupled to inflation port 1014 at a distal end 1020 of inflation tube 1018, whereby inflation tube 1018 may also have an optional flow regulator 1022 positioned relative thereto to regulate the flow and/or pressure of fluid and/or gas in and out of a lumen 1024 of inflation tube 1018 to inflate and deflate expandable balloon 1016. Inflation tube 1018 may further comprise a proximal connector 1026 configured to receive fluid and/or gas from a fluid/gas source (not shown), whereby proximal connector 1026 can be positioned at or near a proximal end 1028 of inflation tube 1018, for example. Inflation of expandable balloon 1016, for example, can be used to anchor first catheter 1000 to a desired position within a luminal organ of a patient.

An exemplary coupler 1012 of the present disclosure further comprises an arterial blood port 1030 configured to receive arterial/oxygenated blood from, for example, an arterial blood tube 1032 coupled thereto at or near a distal end 1034 of arterial blood tube 1032. As shown in FIGS. 15 and 16, a blood flow regulator 1036 may be positioned relative to arterial blood tube 1032 and operate to regulate the flow and/or pressure of arterial/oxygenated blood flow therethrough. In at least one embodiment, blood flow regulator 1036 comprises a rotatable dial capable of rotation to apply and/or remove pressure to/from arterial blood tube 1032 to regulate the flow and/or pressure of blood through a lumen 1038 of arterial blood tube 1032 and/or to adjust pressure therein based upon identified blood pressure measurements. Such a blood flow regulator 1036, for example, can be used to control blood pressure to limit injury to the patient's luminal organs (such as the patient's venous system and/or myocardium) and/or to minimize potential edema with respect to the same luminal organs. Arterial blood tube 1032 may further comprise a proximal connector 1040 configured to receive arterial/oxygenated blood from a blood supply, whereby proximal connector can be positioned at or near a proximal end 1040 of arterial blood tube 1032, for example. A coupler catheter 1042, as shown in the component block diagram of system 100 shown in FIG. 17, may be used to couple arterial blood tube 1032 to a blood supply 1044, which, as described herein, could be a patient's own artery using the patient's heart as a pump, or could be an external supply that provides blood to arterial blood tube 1032, which may then be used in connection with an apparatus to remove blood from the patient as well.

Furthermore, and in at least one embodiment, an exemplary coupler 1012 of the present disclosure further comprises a medicament port 1046 configured to receive a medicament, saline, and/or the like, so that the same can enter the patient by way of first catheter 1000. Medicament port 1046, as shown in FIGS. 15 and 16, may receive a medicament tube 1048 defining a lumen 1050 therethrough, whereby a distal end 1052 of medicament tube 1048 can couple to medicament port 1046 so that a medicament, saline, and/or the like can be introduced from a medicament source (not shown) coupled to medicament tube 1052 at or near a proximal end 1054 of medicament tube 1048. Exemplary medicaments may include, but are not limited to, fibrinolitic drugs, cardiotonic drugs, antirrhytmic drugs, scavengers, cells or angiogenic growth factors, for example, through the coronary vein or another luminal organ. In at least one embodiment, and as shown in FIGS. 15 and 16, medicament tube 1048 can be branched, whereby a second proximal end 1056 of medicament tube 1048 can receive a medicament and control the flow of medicament therethrough, for example, by way of a medicament regulator 1058 positioned relative to medicament tube 1048, for example. Furthermore, one or more of proximal end 1054 and second proximal end 1056 may be configured to receive a wire therein, such as, for example, a 0.035" guidewire and/or a 0.014" pressure wire. As generally referenced herein, any blood, air, fluid, medicament, wire, etc. that enters coupler 1012 by way of inflation port 1014, arterial blood port 1030, and/or medicament port 1046 and eventually enters a lumen of first catheter 1000 will enter one or more of said ports of coupler 1012 and exit outlet port 1013 at the time of entry into first catheter 1000.

Figure 17:
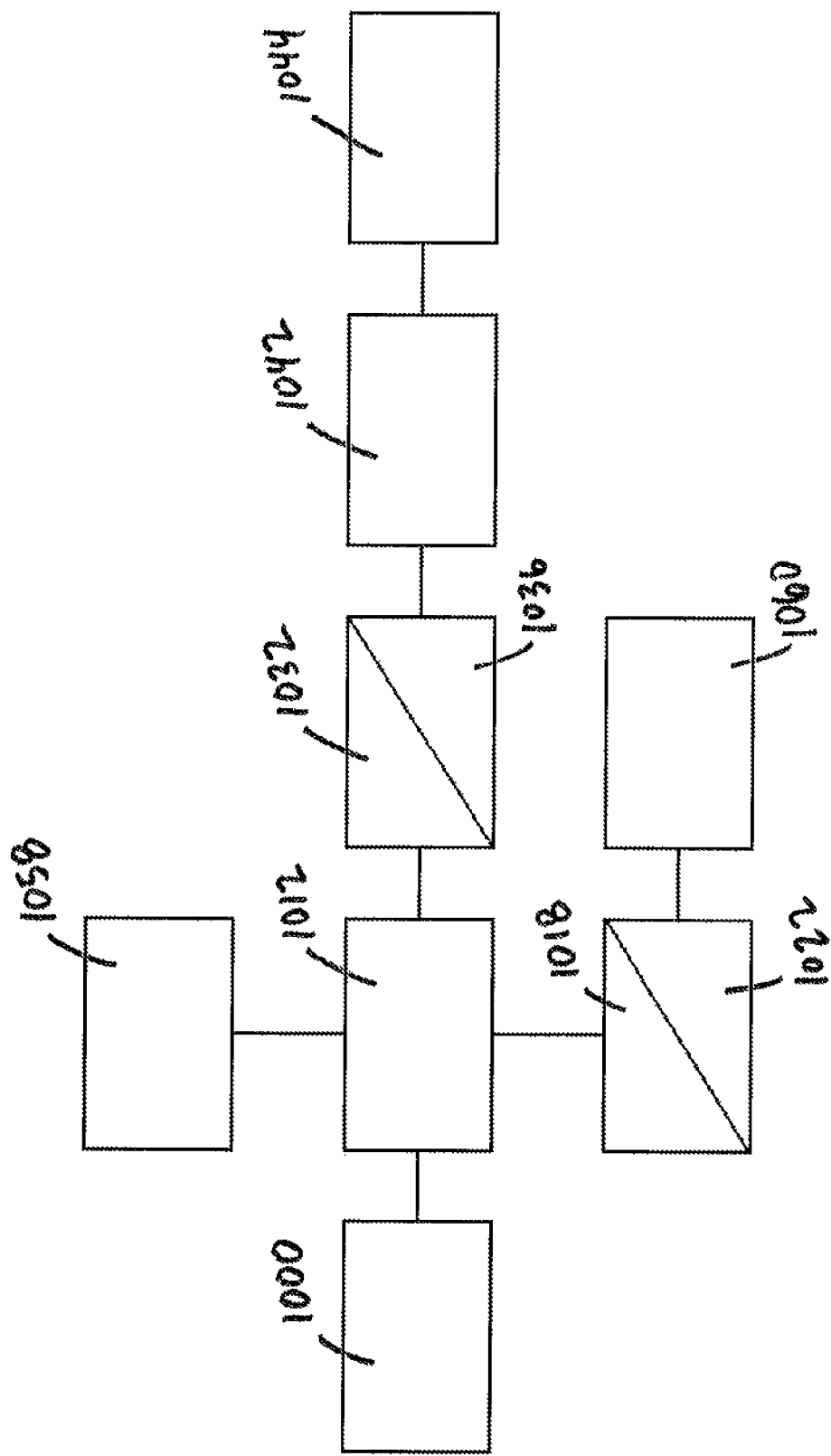
FIG. 17 shows a block diagram of components of an exemplary retroperfusion system coupled to a blood supply, according to at least one embodiment of the present disclosure.

FIG. 17, as referenced above, is a block diagram of various components of an exemplary system 100 of the present disclosure. As shown therein, an exemplary embodiment of a system 100 of the present disclosure comprises a first catheter 1000, a coupler 1012, an arterial blood tube 1032 with a blood flow regulator 1036, and a coupler catheter 1042 configured to for connection to a blood supply 1044, wherein the blood supply may or may not be considered as part of a formal system 100. In addition, an exemplary system 100 may comprise an inflation tube 1018 with a flow regulator 1022, whereby an end of inflation tube 1018 is configured for connection to a gas/liquid source 1060. Various embodiments of systems 100 of the present disclosure may have more or less components than shown in FIG. 17, and exemplary embodiments of systems 100 of the present disclosure may be configured to engage various embodiments of catheters 10 as referenced herein.

In use, for example, first catheter 1000 of system 100 may be positioned within a luminal organ of a patient within the patient's venous system. Inflation of expandable balloon 1016 to secure first catheter 1000 can not only provide oxygenated arterial blood to the patient's venous system, but can also continue to allow coronary venous return to continue due to the selective autoretroperfusion nature of an exemplary embodiment of system 100 and use thereof and due to the redundancy of the patient's venous system. In the event that an increased pressure, edema, or other undesired condition may occur at or near the site of inflated expandable balloon 1016, a user of system 100 could, if desired, temporarily deflate expandable balloon 1016 to allow the increased pressure and or edema to alleviate itself. For example, system 100 could be used for a relatively long period of time (an hour, by way of example), and expandable balloon 1016 could be deflated for a relatively short period of time (seconds, for example), to alleviate a high pressure or edema occurrence, and then expandable balloon 1016 could be re-inflated to again secure first catheter 1000 at a desired location within the patient.

The type of patients for whom the device will be utilized in the acute application may fall into various categories, including, but not limited to, S-T segment Elevated Myocardial Infarction (STEMI) patients, cardiogenic shock patients, and high risk Percutaneous Coronary Intervention (PCI) patients (such as those undergoing PCI of the left main coronary artery). STEMI is the traditional "emergent" patient who presents with classic heart attack symptoms, and when diagnosed in a hospital emergency room for example, the patient would traditionally be immediately moved to a Cath Lab to receive PCI to open an occluded coronary artery and restore blood flow to the myocardium. These patients are hemodynamically unstable and need support for the left ventricle.

In such a use, for example, an exemplary system 100 of the present disclosure could be used to, for example:

(i) provide cardiac support to a patient who does not have immediate access to the Cath Lab and PCI. These patients may present in rural or community hospitals that do not have Cath Labs. They will need some type of temporary support while being transferred to an appropriate facility. These patients might also present at a hospital with a Cath Lab, but the Cath Lab is either understaffed to treat the patient, or does not have an available room to treat. In these cases, the system 100 of the present disclosure operates as a bridge to provide support until definitive treatment (primary PCI) is available; and/or (ii) provide cardiac support before, during, and after primary PCI. Many patients enter the Cath Lab in an unstable condition, and the insertion of balloons and stents adds to hemodynamic instability. An exemplary system 100 can provide cardiac support and improve hemodynamics such that the physician can operate in a more stable/controlled environment. It is also believed that by reperfusing ischemic myocardium before/during/and after primary PCI, one may reduce the amount of myocardium that is damaged by the ischemic event. This is clinically referred to as a "reduction in infarct size." Initial animal studies (as referenced in further detail herein) have suggested that the use of SARP in support of STEMI patients could cause a reduction in infarct size, which would have a significant impact on the outcomes for the patient in both the near and long term. Reduction in infarct size would slow the progression of any subsequent heart failure and reduce long term hospitalization and costs for this group of patients.

Cardiogenic shock is marked by a significant lowering of blood pressure and cardiac output that if not reversed, will ultimately lead to multisystem organ failure and death. Cardiogenic shock patients have a mortality exceeding 60%. In many cases, cardiogenic shock patients are too unstable to undergo surgery or PCI. Pharmacologics are used to increase pressure and cardiac output. Intra Aortic Balloon Pumps (IABP) and other LVAD type products are also employed to improve hemodynamics in an attempt to reverse the downward cycle of cardiogenic shock patients Exemplary embodiments of systems 100 of the present disclosure could be used in much the same fashion.

High Risk PCI is typically defined as patients who have disease of the left main coronary artery, are diabetic, have multivessel disease, are above 75 years of age, have a prior history of MI, have renal insufficiency, etc. These are very sick patients, who are considered at high risk of adverse events before, during, and after undergoing PCI. Mortality rates and Major Adverse Cardiac Event (MACE) rates are much higher in this patient population. IABP's are commonly used in this patient population.

In this population, systems 100 of the present disclosure may be used to provide cardiac support for a high risk PCI patient who is, at the time of the procedure, found to be hemodynamically unstable. It is evident to the operator that cardiac support is and will be needed during the procedure, and an exemplary system 100 of the present disclosure would be deployed from the outset. The patient's hemodynamics improve and the operator feels more comfortable working in the coronary system. IABP use is common in these patients.

Systems 100 of the present disclosure may also be used in this high risk population when it is anticipated that cardiac support may be needed during the procedure. In this case, an exemplary system 100 is deployed prior to the case, in order to provide support when and if it is needed. The patient is hemodynamically stable at the outset, and remains so throughout. IABP's are currently used in this fashion. This is commonly referred to as prophylactic use of cardiac support.

Acute Applications: In this setting, exemplary systems 100 of the present disclosure will be used for cardiac support and to protect myocardium for a period of time that will generally be less than 24 hours. The clinical condition that precipitated the need for SARP will have typically been resolved in that 24 hour period, and the system 100 would be removed. However, use of systems 100 of the present disclosure are not limited to a 24 hour period, as in some cases, IABPs and other short term cardiac support devices are left in for periods exceeding 24 hours. Typically, the longest period of time that a short term device might be left in place is 4-6 days, at which point the clinician would begin to consider longer term implanted Left Ventricular Assist Devices (LVADs), which can support a patient for an extended period of time (weeks), and are often used as a bridge to heart transplant.

Clinical conditions that would require the acute application of an exemplary system 100 of the present disclosure include, but are not limited to:

(i) Emergent treatment of STEMI and/or other Acute Myocardial Infarction (AMI) patients;

(ii) Cardiogenic shock;

(iii) High Risk PCI;

(iv) Failed or aborted PCI where severe hemodynamic instability presents after initiation of the procedure. These patients are often transferred to immediate cardiac surgery, and require cardiac support while waiting for the surgical intervention; and/or (v) Weaning from a cardiopulmonary bypass machine in cardiac surgery. Some cardiac surgery patients have difficulty returning to normal cardiac condition when the cardiopulmonary bypass machine is turned off and the heart is restarted after successful revascularization in cardiac surgery. Exemplary systems 100 of the present disclosure could be used to support the heart until normal cardiac parameters return. Insertion could occur in the surgical suite, and the device would be left in place while the patient was transferred to a Cardiac Critical Care Unit (CCU).

These exemplary clinical conditions cover the majority of potential applications for an acute embodiment of a system 100 of the present disclosure. Currently, more than 95% of all IABP and other short term support devices are used for these applications.

In such applications, the goal of using an exemplary system 100 of the present disclosure is to deliver arterial (oxygenated) blood to the myocardium, in a retrograde manner using the venous system, in order to create hemodynamic stability for the patient and to protect and preserve myocardial tissue until the clinical event resolves or primary intervention (PCI or CABG) and revascularization can occur.

Chronic Applications: In this setting it is intended that an exemplary embodiment of a system 100 of the present disclosure be implanted for 2 weeks or longer, for example, noting that ultimate implantation may be somewhat shorter in duration. Initial animal studies suggest that within 2 weeks, arterialization of the venous system is achieved, such that the venous system can become the conduit for a constant flow of arterial blood at arterial pressure.

A clinical condition where the chronic application of a system 100 would be utilized is often referred to as "no option" patients, that is, patients for which there are no options available through which their clinical condition can be resolved. More specifically, these are patients with diffuse coronary artery disease (CAD) or refractory angina, where PCI and/or Coronary Artery Bypass Graft Surgery (CABG) is not an option. Patients that are diabetic, or have other co-morbidities, and are not candidates for interventions, would be candidates for a chronic application of a system 100 of the present disclosure.

As previously referenced herein, the chronic application will generally require 10-14 days of retroperfusion in order to allow arterialization of the venous system. In certain instances, retroperfusion could be required for a longer period (such as 2-3 weeks, for example), or a lesser period, such as less than 10 days, for example. These patients, dependent upon their complete clinical situation, may be hospitalized for that period, or they may reside outside of the hospital. When residing outside of the hospital, the device utilized may be a catheter 10 embodiment with a branched implantable portion, such as shown in FIG. 1, for example. The catheter 10, including method of pressure regulation, would be implanted in the patient.

For those chronic patients, who must remain in the hospital for one of the aforementioned time periods, an acute embodiment of a system 100, for example, may be applicable. In such an embodiment, for example, system 100 may be percutaneously inserted and utilized during that time frame. Once arterialization occurs, a more permanent conduit may be constructed percutaneously or surgically to provide the permanent arterial blood source.

When using an exemplary system 100 of the present disclosure, standard guide catheters can be used by the clinician to locate the coronary sinus and/or the great cardiac vein, for example. An 0.035" guidewire can be inserted to further establish access to the coronary sinus or the great cardiac vein. An exemplary system 100 can then be inserted over the 0.035" guidewire and advanced to the coronary sinus or the great cardiac vein, for example, via one of the ports as referenced herein.

The distal end 1004 of the first catheter 1000 is intended to be located at the left main vein. The operator may advance the tip (distal end 1014) of first catheter 1000 to other vein sites dependent on clinical need. A balloon 1016, which in at least one embodiment may be located approximately 2 cm back from the distal end 1004, would then be inflated to secure the position of first catheter 1000 within the coronary sinus or the great cardiac vein, for example, allowing for the distal end 1004 of first catheter 1000 to locate at the left main vein. The inflated balloon 1016 will also work to ensure that arterial blood will flow in the retrograde fashion.

Once the distal balloon 1016 is inflated, the 0.035" guidewire can be exchanged for an 0.014" pressure measurement wire, which will be used to measure the pressure at the distal end 1004 of first catheter 1000, to ensure that the portions of system 100 are not over pressurizing the vein, and to tell the operator how much pressure change will be required from the external pressure regulator. The proximal end of the pressure wire will be connected to its appropriate monitor.

When the catheter is located in the coronary sinus or the great cardiac vein, for example, the operator can now make the external (outside the body) connection to the arterial blood supply 1044. This is typically, but not limited to, the femoral or radial arteries. The physician will have previously inserted a standard procedural sheath into the arterial source in order to gain access to the source. This arterial sheath can also be used to provide access for catheters, guidewires, balloons, stents, or other devices that might be utilized while treating the patient. That arterial sheath will have a connector which can connect to the arterial supply cannula (with regulator) on the acute device (an embodiment of system 100). Once the connection is established and flow commences, the pressure wire will indicate the distal pressure measurement and the regulator can be adjusted to the proper setting (not to exceed 60 mmhg, for example). Monitoring of the distal pressure will be on-going throughout the period of time that the device is in-vivo. The regulator allows the operator to provide the correct distal pressures and to adjust those pressures, dependent on changes in the patient's pressure.

With the pressure set and monitored, the patient is now receiving oxygenated blood to the myocardium in a retrograde fashion thru the coronary venous system. Such an operation (namely to retrogradly provide oxygenated blood) can be used to save a significant amount of ischemic tissue at the level of the border zone. In at least one embodiment, such a system 100 is used to perfuse the left anterior descending vein to supply oxygenated blood to the LAD artery occluded territory. Depending upon patient need and circumstance, the acute device (an embodiment of system 100) will be removed typically within the first 24 hours of insertion. The physician will make that determination. The insertion site will be closed per hospital protocol.

Validation of Methodology

As referenced in detail herein, coronary artery disease (CAD) is the number one cause of morbidity and mortality in the U.S. and worldwide. Even today, with percutaneous transluminal coronary angioplasty (PTCA) and coronary artery bypass grafting (CABG), optimal and timely treatment is still not available for all patients. Bridge therapies to complement existing gold standards of reperfusion therapy would be of significant value to a large number of patients.

Because the coronary venous system rarely develops atherosclerosis, the use of the venous system for delivery of oxygenated blood has been well explored. Synchronized retrograde perfusion (SRP) and pressure-controlled intermittent coronary sinus occlusion (PICSO) are two retroperfusion methods for acute treatment of myocardial ischemia through the coronary venous system. PICSO and SRP have been used in conjunction with a balloon-tipped catheter positioned just beyond the orifice of the coronary sinus connected to a pneumatic pump, and either passively redirect coronary sinus blood (PICSO) or actively pump arterial blood during diastole (SRP) to the ischemic myocardium. These techniques have been shown to decrease ischemic changes, infarct size, myocardial hemorrhage, and no-reflow phenomenon, and improve left ventricular (LV) function when coronary blood flow is reinstituted after an acute occlusion. Wide application of these techniques, however, has been limited by concerns over their safety and complexity, and in particular, the need for repeated occlusion of the coronary sinus with a balloon. High pressure (SRP and PICSO) and flow (SRP) can cause damage to the coronary sinus with thrombosis and chronic myocardial edema.

We have validated in animal studies both the acute and chronic application of the methodologies referenced herein. In a recent acute study; we showed that preservation of the contractile function of the ischemic myocardium can be accomplished with selective autoretroperfusion (SARP) without the use of an external pump during acute LAD artery ligation. The hypothesis that SARP can preserve myocardial function at regulated pressures without hemorrhage of vessels or damage of myocytes was verified. In connection with this animal work, a bolus of Heparin was given before instrumentation and was then supplemented as needed to keep an activated clotting time (ACT) over 200 seconds. The right femoral artery was cannulated with a 7 Fr catheter and connected to a pressure transducer (TSD104A—Biopac Systems, Inc) for monitoring of arterial pressure. Before the sternotomy, the right carotid artery was cannulated with a 10 Fr polyethylene catheter through a ventrolateral incision on the neck to reach the brachiocephalic artery to supply the LAD vein during retroperfusion. The catheter had a roller clamp that was used to control the arterial pressure transmitted to the LAD vein. The right jugular vein was cannulated with an 8 Fr catheter for administration of drugs and fluids. Lidocaine hydrochloride was infused at a rate of 60 µg/kg/min before opening the chest and during the rest of the procedure. Magnesium sulfate (10 mg/min IV) along with lidocain was also used to treat extrasystole in the case of the control group. A vasopressor (Levophed®, Norepinephrine Bitartrate Injection, Minneapolis, Minn., 2-6 µg/min IV) was used during the procedure, and was adjusted accordingly to maintain a constant arterial blood pressure (70.0±8.9 mmHg, mean) in both the experimental and the control groups. Finally, heparin and nitroglycerine were diluted in 60 mL of 0.9% sodium chloride and infused using a syringe pump at a rate of 1 ml/min. The chest was opened through a midsternal thoracotomy, and an incision was made in the pericardium with the creation of a sling to support the heart with pericardial stay sutures.

A pair of piezoelectric ultrasonic crystals (2 rpm in diameter on 34 gauge copper wire—Sonometrics Corporation) were implanted through small stab incisions in the anterior wall of the LV (area at risk) distal to the planned site (below first diagonal branch in the SARP group, and second diagonal branch in the control group) of LAD artery ligation, for assessment of regional myocardial function through measurement of midwall segment length changes. An additional pair of crystals was also implanted in the anterior wall of the LV within the normal perfusion bed (control area) of the proximal portion of the LAD artery.

Figure 18:
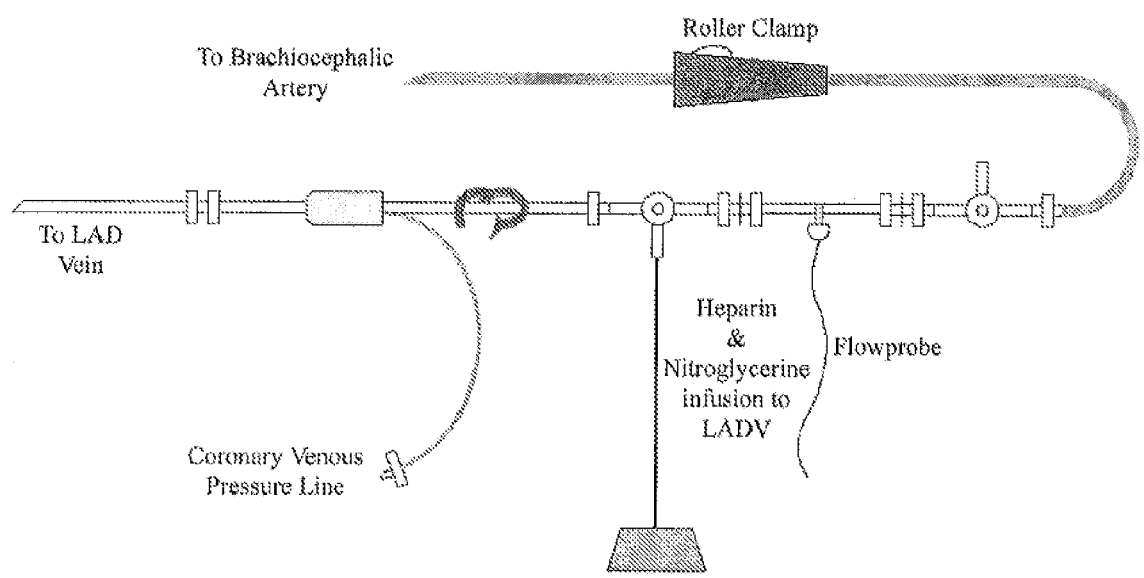
FIG. 18 shows a schematic of the retroperfusion system showing the arterial and retroperfusion catheters, according to a study in connection with the present disclosure.

FIG. 18 shows a schematic of the retroperfusion system showing the arterial and retroperfusion catheters. Each pair of crystals were positioned in the midmyocardium (about 7 mm from the epicardium) approximately 10-15 mm apart and oriented parallel to the minor axis of the heart. The acoustical signal of the crystals was verified by an oscilloscope.

In the SARP group (ligation+retroperfusion) the LAD artery was dissected free from the surrounding tissue distal to the first diagonal branch for subsequent ligation. A 2.5 mm flow probe was placed around the LAD artery and connected to a flow meter (T403—Transonic Systems, Inc). The LAD vein was also dissected close to the junction with the great cardiac vein, and the proximal portion ligated with 2-0 silk suture in order to prevent runoff to the coronary sinus. The LAD vein was then cannulated below the ligation with a 10 Fr cannula that was attached to the brachiocephalic catheter through one of two four-way stopcocks. A flow probe was placed between the stopcocks for measurement of coronary venous flow. Venous pressure was recorded through the pressure monitoring line from the retroperfusion cannula (as shown in FIG. 18). Retroperfusion was initiated immediately after ligation of the LAD artery and was maintained for a period of 3 hours. Arterial blood samples were taken at baseline and at the end of the first, second and third hours of ligation+retroperfusion for monitoring of pH, hematocrit, electrolytes, activated clotting time, and cardiac troponin I.

Coronary venous SARP may be an effective method of protecting the myocardium during acute ischemia before definitive treatment is established as referenced herein regarding various catheter 10 and system 100 embodiments of the present disclosure. SARP may not only offer protection to the ischemic myocardium through retrograde perfusion of oxygenated blood but may also serve as a route for administration of thrombolytics, antiarrhythmics, and cell and gene therapy to the jeopardized myocardium before PTCA or CABG can be implemented in patients eligible for these procedures.

In addition to the foregoing, various devices and systems of the present disclosure can be used to perform methods for retroperfusion of various bodily organs to treat many different types of conditions. As referenced above, providing blood from one bodily vessel to another bodily vessel can be performed using devices and systems of the present disclosure, but in accordance with the following, said devices and systems can also be used to perform the following novel methods and procedures.

As generally referenced above, the concept of using veins to deliver oxygenated nutrient-filled blood (arterial blood) is predicated on the fact that despite any extent of the coronary arterial disease, the corresponding venous counterpart is atherosclerosis-free. An additional fact is that the upper body arterial system has much less predilection for atherosclerosis than the lower body. As such, the present disclosure identifies that the upper body can generally serve as the source of arterial blood to the venous systems of organs with arterial disease, and that devices and systems of the present disclosure can also be used in that regard.

An additional characteristic of the venous system necessary to facilitate SARP (as referenced herein) is the existence of a redundancy of the venous system (namely multiple veins per artery as well as interconnections between venous vessels) to ensure proper venous drainage when portion of the system is used for SARP.

In view of the foregoing, a number of embodiments for retroperfusion of various organs or bodily regions that identify arterial blood donor and organ (venous system) are identified with the present disclosure, including, but not limited to, the following:

(i). Peripheral vessels. Embodiments of devices and systems of the present disclosure can be used to provide oxygenated blood from the femoral artery, the internal femoral artery, or the iliac artery, for example, to the distal saphenous vein or to deep muscle veins for arterialization in diabetic patients (a diffuse disease) to treat, for example a leg pre-amputation or a necrotic or gangrenous foot ulcer. This venous system has valves (typically larger than 1-1.5 mm in diameter) which can be overcome (inverted) through catheterization (namely the insertion of guidewire and SARP catheter, with guidewire dimensions down to 0.35 mm for 0.014" standard guidewire) to facilitate said peripheral vessel treatment.

(ii). Kidney-Renal Vein. Embodiments of devices and systems of the present disclosure can also be used to facilitate arterialization of the renal vein, which can be partial (polar vein) or total (left or right main veins) by way of the femoral or iliac arteries (if disease free), or from the axillary, brachial, or subclavian arteries of the upper body, if desired. Said procedure could be performed to, for example, treat acute or chronic renal ischemia due to diffuse atherosclerosis, severe intima hyperplasia, and to treat the kidney in connection with various collagen-vascular diseases.

(iii). Intestine (Bowel). A number of arterial sources, such as the femoral, iliac, axiallary, brachial, subclavian, or epigastric arteries, can be used with devices and systems of the present disclosure to facilitate regional arterialization following vein anastomosis (at the vein arch) to treat mesenteric arterial ischemia. In at least one embodiment, said arterialization is performed to treat an acute embolic or thrombotic mesenteric artery occlusion in patients with a severe bowel ischemia.

(iv). Spine. The first of the two main divisions of the spinal system, namely the intracranial veins, includes the cortical veins, the dural sinuses, the cavernous sinuses, and the ophthalmic veins. The second main division, namely the vertebral venous system (VVS), includes the vertebral venous plexuses which course along the entire length of the spine. The intracranial veins richly anastomose with the VVS in the suboccipital region, and caudally, the cerebrospinal venous system (CSVS) freely communicates with the sacral and pelvic veins and the prostatic venous plexus. The CSVS constitutes a unique, large-capacity, valve-less venous network in which flow is bidirectional. The CSVS plays important roles in the regulation of intracranial pressure with changes in posture, and in venous outflow from the brain. In addition, the CSVS provides a direct vascular route for the spread of a tumor, an infection, or an emboli among its different components in either direction. Various embodiments of devices and systems of the present disclosure can be used to provide oxygenated blood from the external carotid artery, the brachial artery, or the axiallary artery, directly to the jugular vein to treat any number of potential spinal injuries or conditions, including spinal cord ischemia.

(v). Penis. Various embodiments of devices and systems of the present disclosure can also be used to provide arterial blood from the epigastric artery to the penile dorsal vein to the cavernous system of the penis to treat erectile dysfunction.

The foregoing examples of organ-specific perfusion protocols are not intended to be exhaustive, but merely exemplary of various novel uses of perfusion devices and systems of the present disclosure. Accordingly, the present disclosure includes various methods for treating organ-related diseases, various methods of providing arterial (oxygenated) blood to veins at or near various organs, and various methods of potentially arterializing veins at or near various bodily organs using devices and systems of the present disclosure.

Figure 19:
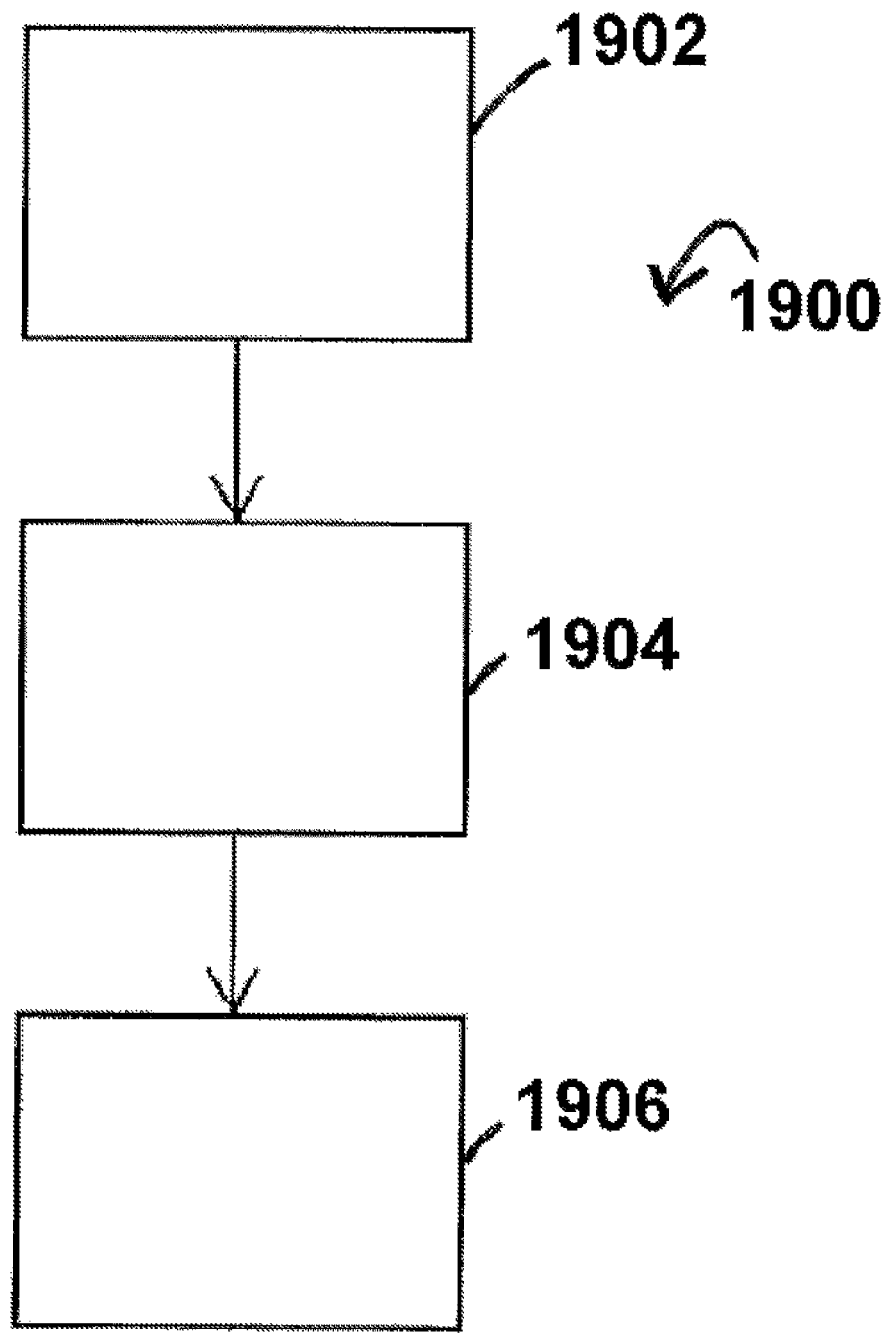
FIG. 19 shows a diagram of steps of an exemplary method of organ perfusion, according to at least one embodiment of the present disclosure.

For example, and as shown in FIG. 19, an exemplary method of organ perfusion of the present disclosure is provided. Method 1900, in at least one embodiment, comprises the steps of positioning at least a portion of a device into a patient's artery (an exemplary artery positioning step 1902), positioning at least a portion of the same or a different device into a patient's vein at or near a target organ (an exemplary vein positioning step 1904), and facilitating operation of the positioned portions to allow blood to flow from the artery to the vein to treat a condition or disease of the target organ (an exemplary operation step 1906).

By way of example, an exemplary artery positioning step 1902 could be performed by positioning at least part of a first catheter 10 having a cannula 16 within an artery of a patient, the first catheter 10 configured to permit arterial blood to flow therethrough and further configured to permit a portion of the arterial blood to flow through the cannula 16, and an exemplary vein positioning step 1904 could be performed by positioning at least part of a second catheter 150 within a vein of the patient at or near a target organ, the second catheter 150 configured to receive some or all of the portion of the arterial blood. In such an embodiment, which may be referred to as a chronic treatment using catheter 10 and catheter 150, an exemplary operation step 1906 involves connecting the cannula 16 of the first catheter 10 to a portion of the second catheter 150 so that some or all of the portion of the arterial blood flowing through the cannula 16 is provided into the vein to treat a condition or disease of the target organ.

Further, and by way of another example, an exemplary artery positioning step 1902 could be performed by positioning at least a portion of an arterial tube 1032 of a perfusion system 100 within an artery of a patient, the arterial tube 1032 configured to permit arterial blood to flow therethrough, and an exemplary vein positioning step 1904 could be performed by positioning at least a portion of a first catheter 1000 of the perfusion system 100 into a vein of the patient at or near a target organ, the first catheter 1000 configured to receive some or all of the arterial blood from the arterial tube 1032. In such an embodiment, which may be referred to as an acute treatment using system 100 of the present disclosure, an exemplary operation step 1906 involves operating a first flow regulator 1036 of the perfusion system 100 so that some or all of the arterial blood flowing through the arterial tube 1032 is provided into the vein to treat a condition or disease of the target organ.

While various embodiments of retroperfusion devices and systems and methods for using the same have been described in considerable detail herein, the embodiments are merely offered by way of non-limiting examples of the disclosure described herein. It will therefore be understood that various changes and modifications may be made, and equivalents may be substituted for elements thereof, without departing from the scope of the disclosure. Indeed, this disclosure is not intended to be exhaustive or to limit the scope of the disclosure. Further, in describing representative embodiments, the disclosure may have presented a method and/or process as a particular sequence of steps. However, to the extent that the method or process does not rely on the particular order of steps set forth herein, the method or process should not be limited to the particular sequence of steps described. Other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A method of organ perfusion, the method comprising the steps of:
   positioning at least part of a first catheter having a cannula within an artery of a patient, the first catheter configured to permit arterial blood having a pressure to flow therethrough and further configured to permit a portion of the arterial blood to flow through the cannula;
   positioning at least part of a second catheter within a vein of the patient at or near a target organ, the second catheter configured to receive some or all of the portion of the arterial blood;
   directly connecting the cannula of the first catheter to a portion of the second catheter, while a heart of the patient is pumping blood, so that some or all of the portion of the arterial blood flowing through the cannula is provided into the vein to treat a condition or disease of the target organ, wherein said arterial blood flows through the cannula due to pumping of the patient's heart and without the use of a secondary pump;
   regulating the pressure of the arterial blood flowing into the vein; and
   wherein the method further comprises the step of modifying the pressure of the arterial blood flowing into the vein to achieve arterialization over time.

2. The method of claim 1, wherein the step of positioning at least part of the first catheter is performed by positioning at least part of the first catheter within an artery selected from the group consisting of a femoral artery, an internal femoral artery, and an iliac artery.

3. The method of claim 2, wherein the step of positioning at least part of the second catheter is performed by positioning at least part of the second catheter within a vein selected from the group consisting of a distal saphenous vein and a deep muscle vein.

4. The method of claim 3, wherein the step of connecting the cannula to the portion of the second catheter is performed to permit blood flow from the cannula to the vein to treat a diabetic condition.

5. The method of claim 1, wherein the step of positioning at least part of the first catheter is performed by positioning at least part of the first catheter within an artery selected from the group consisting of a femoral artery, an internal femoral artery, an iliac artery, an axillary artery, a brachial artery, and a subclavian artery; and
   wherein the step of regulating the pressure of the arterial blood flowing into the vein is performed by operation of a flow regulator selected from the group consisting of a rotatable dial, an external compression device, a coil configured to at least partially occlude the vein, and an inflatable or resorbable stenosis.

6. The method of claim 5, wherein the step of positioning at least part of the second catheter is performed by positioning at least part of the second catheter within a renal vein, and wherein the step of connecting the cannula to the portion of the second catheter is performed to permit blood flow from the cannula to the vein to treat a kidney condition.

7. The method of claim 1, wherein the step of positioning at least part of the first catheter is performed by positioning at least part of the first catheter within an artery selected from the group consisting of a femoral artery, an internal femoral artery, an iliac artery, an axillary artery, a brachial artery, and an epigastric artery.

8. The method of claim 7, wherein the step of positioning at least part of the second catheter is performed by positioning at least part of the second catheter within a mesenteric vein, and wherein the step of connecting the cannula to the portion of the second catheter is performed to permit blood flow from the cannula to the vein to treat an intestinal condition.

9. The method of claim 1, wherein the step of positioning at least part of the first catheter is performed by positioning at least part of the first catheter within an artery selected from the group consisting of an external carotid artery, a brachial artery, and an axillary artery.

10. The method of claim 9, wherein the step of positioning at least part of the second catheter is performed by positioning at least part of the second catheter within a jugular vein.

11. The method of claim 10, wherein the step of connecting the cannula to the portion of the second catheter is performed to permit blood flow from the cannula to the vein to treat a spinal condition.

12. The method of claim 1, wherein the step of positioning at least part of the first catheter is performed by positioning at least part of the first catheter within an epigastric artery.

13. The method of claim 12, wherein the step of positioning at least part of the second catheter is performed by positioning at least part of the second catheter within a penile dorsal vein, and wherein the step of connecting the cannula to the portion of the second catheter is performed to permit blood flow from the cannula to the vein to treat a penile condition.

14. A method of organ perfusion, the method comprising the steps of:

positioning at least a portion of an arterial tube of a perfusion system within an artery of a patient, the arterial tube configured to permit arterial blood having a first pressure to flow therethrough;

positioning at least a portion of a first catheter of the perfusion system into a vein of the patient at or near a target organ and directly connecting the first catheter to the arterial tube, the first catheter configured to receive some or all of the arterial blood from the arterial tube; and operating a first flow regulator of the perfusion system to regulate the pressure of the arterial blood flowing into the vein, while a heart of the patient is pumping blood, so that some or all of the arterial blood flowing through the arterial tube is provided into the vein at a second pressure to treat a condition or disease of the target organ, wherein said arterial blood flows through the arterial tube due to pumping of the patient's heart and without the use of a secondary pump; and wherein the method further comprises the step of modifying the pressure of the arterial blood flowing into the vein to achieve arterialization over time.

15. The method of claim 14, wherein the step of positioning at least part of the arterial tube is performed by positioning at least part of the arterial tube within an artery selected from the group consisting of a femoral artery, an internal femoral artery, an iliac artery, an axillary artery, a brachial artery, a subclavian artery, an epigastric artery, and an external carotid artery.

16. The method of claim 15, wherein the step of operating a first flow regulator is performed to permit blood flow from the cannula to the vein to treat a condition selected from the group consisting of a diabetic condition, a kidney condition, an intestinal condition, a spinal condition, and a penile condition.

17. The method of claim 14, wherein the step of positioning at least a portion of a first catheter further comprises the step of inflating an expandable balloon positioned along the portion of the first catheter positioned in the vein to secure the portion of the first catheter within the vein.

18. The method of claim 14, wherein the step of positioning at least a portion of an arterial tube further comprises the step of operating the first flow regulator to regulate blood flow from the artery to the vein prior to the step of positioning at least a portion of a first catheter so to substantially eliminate an introduction of a gas within at least a portion of the perfusion system to the vein.

19. The method of claim 14, further comprising the step of: removing the at least a portion of a first catheter from the vein after an elapsed period of time after positioning the at least a portion of a first catheter into the vein, the elapsed period of time selected from the group consisting of within 24 hours, between 24 hours and 48 hours, and after out 48 hours.

20. The method of claim 14, wherein the step of operating a first flow regulator of the perfusion system is performed to limit potential injury to the vein of the patient.

21. The method of claim 14, wherein the step of positioning at least a portion of a first catheter is performed to position the first catheter at a location so not to impede coronary venous return; and wherein the method further comprises the step of operating the first flow regulator to modify the second pressure of the arterial blood to achieve arterialization of the vein over time.

22. The method of claim 17, further comprising the step of: temporarily deflating the expandable balloon during operation of the system to alleviate a localized increase in pressure or edema at or near the expandable balloon an artery selected from the group consisting of a femoral artery, an internal femoral artery, and an iliac artery, and wherein the first flow regulator is selected from the group consisting of a rotatable dial, an external compression device, a coil configured to at least partially occlude the vein, and an inflatable or resorbable stenosis.

23. A method of organ perfusion, the method comprising the steps of:

positioning at least a portion of an arterial tube of a perfusion system within an artery of a patient, the arterial tube configured to permit arterial blood having a pressure to flow therethrough;

positioning at least a portion of a first catheter of the perfusion system into a vein of the patient at or near a target organ and directly connecting the first catheter to the arterial tube, the first catheter configured to receive some or all of the arterial blood from the arterial tube; and inflating an expandable balloon positioned along the portion of the first catheter positioned in the vein to secure the portion of the first catheter within the vein; and operating a first flow regulator of the perfusion system to regulate the pressure of the arterial blood flowing into the vein, while a heart of the patient is pumping blood, so that some or all of the arterial blood flowing through the arterial tube is provided into the vein to treat a condition or disease of the target organ, wherein said arterial blood flows through the arterial tube due to pumping of the patient's heart and without the use of a secondary pump;

wherein the step of positioning at least part of the arterial tube is performed by positioning at least part of the arterial tube within an artery selected from the group consisting of a femoral artery, an internal femoral artery, an iliac artery, an axillary artery, a brachial artery, a subclavian artery, an epigastric artery, an external carotid artery; and wherein the step of operating a first flow regulator is performed to permit blood flow from the cannula to the vein to treat a condition selected from the group consisting of a diabetic condition, a kidney condition, an intestinal condition, a spinal condition, and a penile condition; and wherein the method further comprises the step of modifying the pressure of the arterial blood flowing into the vein to achieve arterialization over time.

* * * * *